«12» United States Patent
Kleinstern et al.

(10) Patent No.: US 12,186,490 B2
(45) Date of Patent: Jan. 7, 2025

(54) THREE-WAY VALVE AND PATIENT CIRCUIT ADAPTOR FOR A MEDICAL VENTILATOR

(71) Applicant: Flight Medical Innovations Ltd., Petach-Tikva (IL)

(72) Inventors: Amir Kleinstern, Kiryat-Ono (IL); Nitzan Hirsh, Tel Aviv (IL); Yossi Halfon, Givon HaHadasha (IL)

(73) Assignee: Flight Medical Innovations Ltd., Petach-Tikva (IL)

( * ) Notice: Subject to any disclaimer, the term of this patent is extended or adjusted under 35 U.S.C. 154(b) by 1211 days.

(21) Appl. No.: 16/756,132

(22) PCT Filed: Nov. 8, 2018

(86) PCT No.: PCT/IL2018/051206
§ 371 (c)(1),
(2) Date: Apr. 15, 2020

(87) PCT Pub. No.: WO2019/092716
PCT Pub. Date: May 16, 2019

(65) Prior Publication Data
US 2020/0238044 A1 Jul. 30, 2020

Related U.S. Application Data

(60) Provisional application No. 62/582,982, filed on Nov. 8, 2017.

(51) Int. Cl.
*A61M 16/20* (2006.01)
*A61M 16/00* (2006.01)
*A61M 16/08* (2006.01)

(52) U.S. Cl.
CPC ...... *A61M 16/205* (2014.02); *A61M 16/0875* (2013.01); *A61M 2016/0027* (2013.01);
(Continued)

(58) Field of Classification Search
CPC ............ A61M 16/205; A61M 16/0875; A61M 16/0858; A61M 16/085; A61M 16/20;
(Continued)

(56) References Cited

U.S. PATENT DOCUMENTS 3,831,599 A 8/1974 Needham
9,205,221 B2 12/2015 Winter et al.
(Continued)

FOREIGN PATENT DOCUMENTS

EP 0878207 11/1998
WO WO 2019/092716 5/2019

OTHER PUBLICATIONS

Office Action Dated May 9, 2023 From the Israel Patent Office Re. Application No. 274192. (4 Pages).
(Continued)

*Primary Examiner* — Kendra D Carter
*Assistant Examiner* — Maap Ahmed Ellabib

(57) ABSTRACT

A ventilator console includes an inhalation port, an exhalation port, a console sampler to sample pressure or flow at the exhalation port and at least one sensor to sense at least one of pressure and flow velocity. The ventilator console additionally includes at least one external control port that provides an interface for flow or pressure communication between the at least one sensor and a tube connected to a patient circuit and a three-way valve integrated into the at least one external control port. The three-way valve is connected to the at least one sensor via a common port and toggles between establishing flow or pressure communication to the console sampler and establishing flow or pressure communication to the external control port.

24 Claims, 19 Drawing Sheets

(52) U.S. Cl.
CPC . *A61M 2016/0042* (2013.01); *A61M 16/0858* (2014.02); *A61M 2205/123* (2013.01)

(58) Field of Classification Search
CPC .. A61M 2016/0027; A61M 2016/0042; A61M 2205/123; A61M 16/0057
See application file for complete search history.

(56) References Cited

U.S. PATENT DOCUMENTS

| | | |
|---|---|---|
| 2011/0146681 A1 | 6/2011 | Jafari et al. |
| 2016/0166789 A1* | 6/2016 | Enk .................. A61M 16/0096 128/204.25 |
| 2017/0074845 A1 | 3/2017 | Tolmie et al. |

OTHER PUBLICATIONS

Communication Pursuant to Article 94(3) EPC Dated May 17, 2023 From the European Patent Office Re. Application No. 18808521.1 (5 Pages).

International Preliminary Report on Patentability Dated May 22, 2020 From the International Bureau of WIPO Re. Application No. PCT/IL2018/051206. (10 Pages).

International Search Report and the Written Opinion Dated Jan. 28, 2019 From the International Searching Authority Re. Application No. PCT/IL2018/051206. (17 Pages).

* cited by examiner

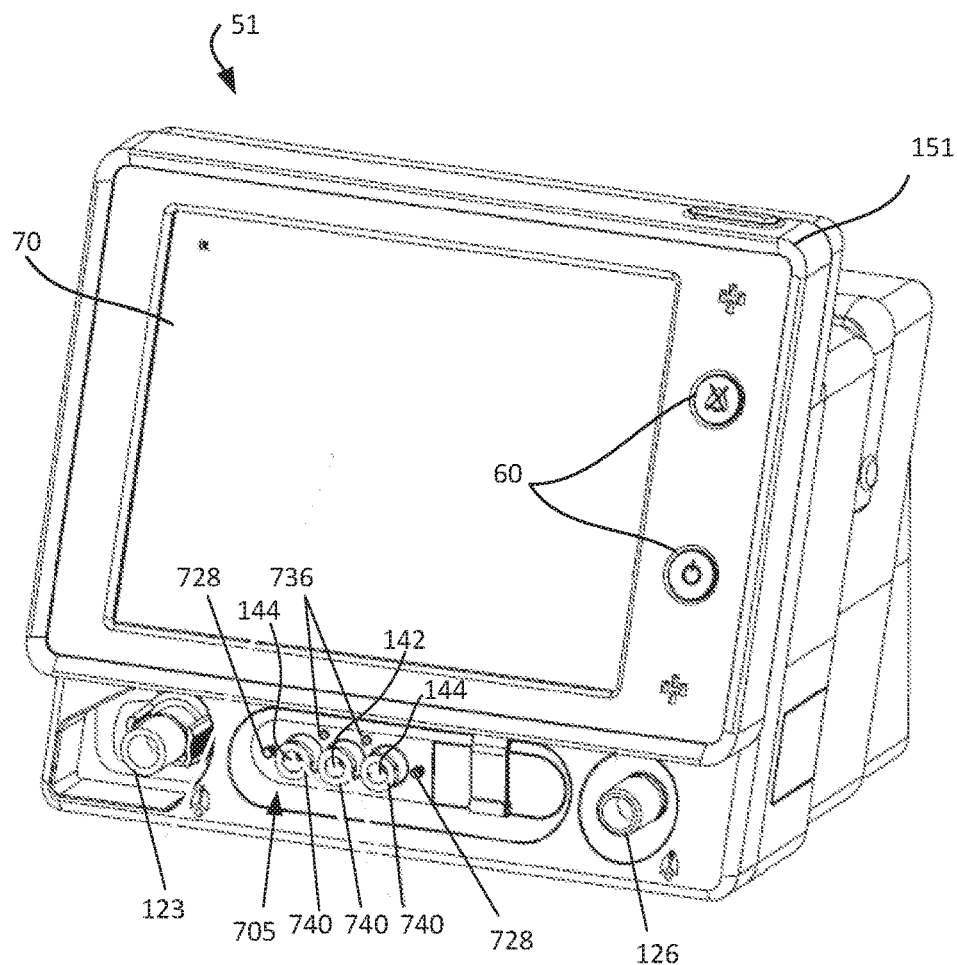
FIG. 9A
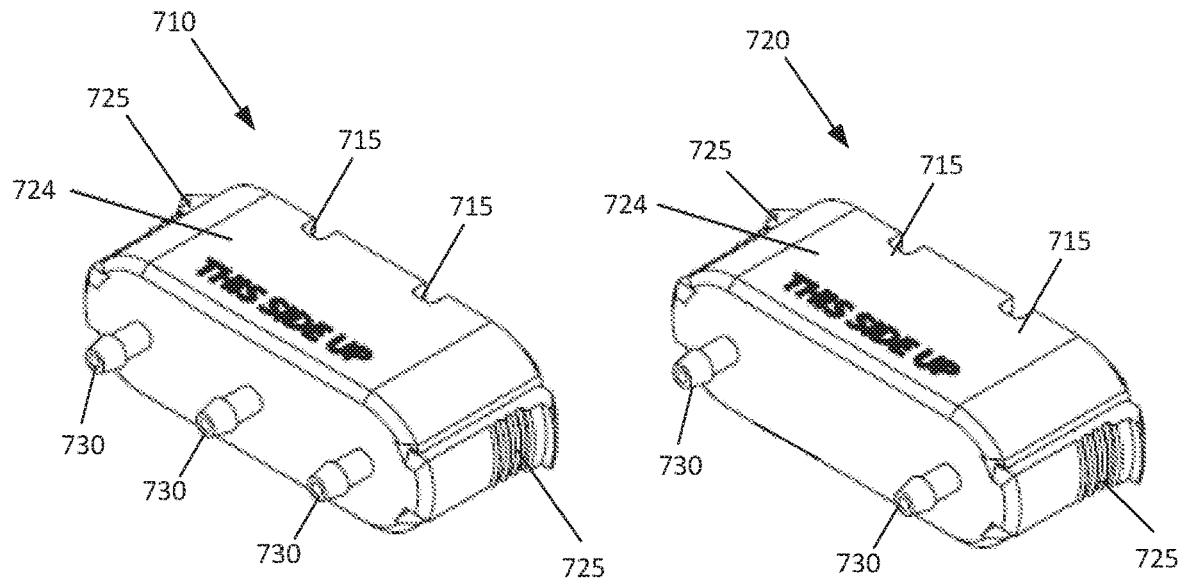
FIG. 9B
FIG. 9C

THREE-WAY VALVE AND PATIENT CIRCUIT ADAPTOR FOR A MEDICAL VENTILATOR

RELATED APPLICATIONS

This application is a National Phase of PCT Patent Application No. PCT/IL2018/051206 having International filing date of Nov. 8, 2018, which claims the benefit of priority under 35 USC § 119 (e) of U.S. Provisional Patent Application No. 62/582,982 filed on Nov. 8, 2017. The contents of the above applications are all incorporated by reference as if fully set forth herein in their entirety.

FIELD AND BACKGROUND OF THE INVENTION

The present invention, in some embodiments thereof, relates to a medical ventilator and, more particularly, but not exclusively, to a patient circuit for a medical ventilator.

Ventilators are used in a variety of settings as part of a patient's medical care. For example, a patient may be ventilated in a hospital, in home care or in emergency medicine setting. A ventilator may also be used as a component of an anesthesia machine. Ventilators are electronically controlled to allow exact adaptation of pressure and flow characteristics to an individual patient's needs. Fine-tuned ventilator settings may also serve to make ventilation more tolerable and comfortable for the patient.

A patient circuit (or a breathing circuit) provides air flow communication between the ventilator console and the patient. The patient circuit is connected either noninvasively or invasively to the patient at one end and to a plurality of ports on a ventilator console at an opposite end. Typically, two of the patient circuit connector ports on the ventilator are used for pressure and flow sensing and one is a diaphragm pressure port. Depending on the selected patient circuit, pressure and flow parameters may be sensed and controlled based on internal pneumatic measurement, e.g. control points from within the ventilator, or based on external measurement, e.g. control points positioned outside the console via one or more of the tubes connected to the ports on the console to get better measurements accuracy. The operator may select a patient circuit based on interfacing with an electronic display and selecting buttons or dials on the console. A patient circuit may be single-limbed or dual-limbed. A single limb patient circuit has its own exhalation valve and the ventilator controls the exhalation valve by supplying pressurized air to the exhalation valve membrane in the patient circuit.

SUMMARY OF THE INVENTION

One of the ergonomic challenges in operating a medical ventilator is related to the speed and ease at which an operator may connect a patient to the ventilator with a suitable patient circuit. Over the course of patient ventilation or while connecting a new patient to the ventilator, the operator may need to switch to a different type of patient circuit. Connecting and configuring a suitable patient circuit may be time consuming, may require familiarity with the physical and user interface features of the console and may lead to confusion, especially in emergency situations. While the operator is setting up the patient circuit, the patient may suffer from lack of ventilation.

According to example embodiments, there is provided a ventilator that can switch between patient circuits based on direct pneumatic switching without having to interface with an electronic display and select buttons or dials on the console. In some example embodiments, an operator may select a patient circuit by plugging the tubes into the console that are required for the patient circuit and unplugging the tubes from the console that are not required by the patient circuit. The mechanical act of the plugging and unplugging configures the console to the selected patient circuit. Switching between patient circuits based on plugging and unplugging the tubes may be both intuitive and quick. Furthermore, the patient circuit that is being used may be readily apparent based on the connections that have been made.

According to some example embodiments, there is provided a dedicated patient circuit adaptor for each type of patient circuit and the patient circuit may be actuated based on plugging the dedicated adaptor to the ventilator console. According to some example embodiments, the ventilator console is adapted to operate with a patient circuit adaptor. Each adaptor includes only the tube connections required for the designated patient circuit. The tubes may be connected to the patient circuit adaptor before or after connecting the patient circuit adaptor to the ventilator console.

According to an aspect of some example embodiments there is provided a ventilator console comprising: an inhalation port via which gas is delivered to the patient; an exhalation port via which gas exhaled from a patient is received; a console sampler configured to sample pressure or flow at the exhalation port; at least one sensor configured to sense at least one of pressure and flow velocity; at least one external control port configured to provide an interface for flow or pressure communication between the at least one sensor and a tube connected to a patient circuit; and a three-way valve integrated into the at least one external control port, wherein the three-way valve is connected to the at least one sensor via a common port and is configured to toggle between establishing flow or pressure communication to the console sampler and establishing flow or pressure communication to the an external control port, wherein the three-way valve is configured to be mechanically actuated based on pushing or releasing the three-way valve against a spring force.

Optionally, the at least one external control port includes a sensor port, wherein the three-way valve includes a default position and an actuated position and wherein the three-way valve is configured to provide flow or pressure communication between the at least one sensor and the console sampler in the default position.

Optionally, the at least one external control port includes a sensor port, wherein the three-way valve includes a default position and an actuated position and wherein the three-way valve is configured to provide flow or pressure communication between the at least one sensor and an external sampler in the actuated position.

Optionally, the at least one external control port includes a pair of sensing ports and wherein the at least one sensor includes a delta pressure sensor and pressure sensor and wherein each of the sensing ports includes the three-way valve.

Optionally, each of the three-way valves in the pair includes an element with a unique shape that is configured to provide a dedicated connection between its dedicated tube connector.

Optionally, the toggling is actuated based on plugging or unplugging a dedicated tube connector of the three-way valve into the at least one external control port.

Optionally, the ventilator console further including a pressurized air source; an internal exhalation valve configured to be controlled with the pressurized air source; a diaphragm pressure port configured to provide an interface for flow or pressure communication between an external exhalation valve and the pressurized air source; and an additional three-way valve integrated with the diaphragm pressure port, wherein the additional three-way valve is connected to the pressurized air source via its common port and is configured to toggle between establishing pressure or flow communication with the internal exhalation valve and establishing pressure or flow communication with the external exhalation valve, wherein the toggling is actuated based on plugging or unplugging a tube connector dedicated to the diaphragm pressure port.

Optionally, the ventilator console further including a pressurized air source; an internal exhalation valve configured to be controlled with the pressurized air source; a diaphragm pressure port configured to provide an interface for flow or pressure communication between an external exhalation valve and the pressurized air source; and an additional three-way valve integrated with the diaphragm pressure port, wherein the additional three-way valve is connected to the pressurized air source via its common port and is configured to toggle between establishing pressure or flow communication with the internal exhalation valve and establishing pressure or flow communication with the external exhalation valve, wherein the toggling of the a three-way valve and the additional three-way valve is based on plugging or unplugging a dedicated adaptor configured to selectively toggle the three-way valve and the additional three-way valve, wherein the selective toggling is of all the three-way valves is performed simultaneously based on the plugging or the unplugging of the dedicated adaptor.

Optionally, the at least one external control port includes two external control ports each housing a three-way valve and wherein the adaptor is configured to simultaneously toggle the three-way valve in each of the two external control ports.

Optionally, the ventilator console further including a console controller, wherein the console controller is configured to automatically switch without user intervention between internally and externally controlled breathing based on sensing toggling of the three-way valve.

According to an aspect of some example embodiments there is provided a three-way valve for a medical ventilator comprising: a housing integrated with a control port on a console of the ventilator, wherein the housing includes a common port and a port A; a piston fitted into the housing with an O-ring and configured to move in and out of the housing, wherein the piston includes a piston central drill and a side opening connected to the piston central drill; wherein the three-way valve is configured to provide pressure or flow communication between the common port and port A as long as the piston is displaced from the common port and to provide pressure or flow communication between the common port and the piston central drill (port B) based on the piston being pushed into the housing and overlapping with the common port.

Optionally the three-way valve further including a tube connector configured to removably connect to the piston, wherein the tube connector includes a tube central drill that is configured to fluidly connect to the piston central drill.

Optionally, the tube connector is configured to push the piston into the housing based on plugging the tube connector into the control port.

Optionally, the three-way valve further including a bayonet connector configured to lock the tube connector into the control port.

Optionally, the tube connector is integrated with a male part of the bayonet connector and wherein the female part of the bayonet connector is attached to the housing.

Optionally, the three-way valve is configured to be mechanically operated based on plugging and unplugging the tube connector into the control port.

Optionally, the three-way valve further including an adaptor including a plurality of tube connectors coupled to a plurality of male connectors and wherein one of the male connectors is configured is configured to push the piston into the housing based on plugging the adaptor into the control port.

Optionally, the three-way valve is configured to be mechanically operated based on plugging and unplugging the adaptor into the control port.

Optionally, the three-way valve further including a spring housed in the housing and wherein the spring is configured to provide a spring force against the piston moving into the housing.

Optionally, the piston is fitted into the housing with a pair of O-rings, the pair of O-ring positioned on opposite sides of the side opening.

Optionally, the three-way valve is configured to toggle between controlling pressure or flow based on internal sampling from within the console and external pressure or flow sampling with a patient circuit.

Optionally, the three-way valve is configured to toggle between controlling an exhalation valve internal to the console and exhalation valve external to the console.

According to an aspect of some example embodiments there is provided a method for operating a medical ventilator, the method comprising: selectively plugging in a pair of tube connectors to a pair of flow sensor ports in a ventilator console; selectively plugging in a third tube connector to a pneumatic diaphragm pressure port on the ventilator console; operating the ventilator based on external pressure or flow measurements as long as the pair of tube connectors is plugged into sensing ports; operating the ventilator based on internal pressure or flow measurements as long as the pair of tube connectors is unplugged to the sensing ports; operating the ventilator based on an external exhalation valve as long as the third tube connector is plugged into the pneumatic diaphragm pressure port; operating the ventilator based on an internal exhalation valve as long as the pair of tube connectors is unplugged to the pneumatic diaphragm pressure port; wherein switching between the different modes of operation is actuated based on the plugging and the unplugging and without interfacing with an electronic display and selecting buttons or dials on the console.

Optionally, the switching is performed during ventilation without interrupting the ventilation.

Optionally, the tube connectors are connected to tubes on a patient circuit.

According to an aspect of some example embodiments there is provided an adaptor for operating a medical ventilator, comprising: a housing configured to be clipped onto a ventilator console; at least two tube connectors extending from the housing; at least two male connectors including a central drill, wherein each of the at least two male connectors is fluidly connected to one of the at least two tube connectors and wherein each of the at least two male connectors is configured to penetrate into a port on the ventilator console based on clipping the housing onto a ventilator console.

Optionally, the at least two male connectors are positioned to penetrate into a pair of sensing ports and to actuate external sensing based on clipping the housing onto the ventilator console.

Optionally, the adaptor is configured to actuate a dual-limb patient circuit based on clipping the housing to the ventilator console.

Optionally, the at least two male connectors includes a third male connector fluidly connected to a third tube connector and wherein the third male connector is positioned to penetrate into pneumatic diaphragm pressure port based on clipping the housing to the ventilator console.

Optionally, the adaptor is configured to actuate a single-limb patient circuit based on clipping the housing onto the ventilator console.

Optionally, the adaptor further includes a mechanical feature configured to restrict clipping of the adaptor onto ventilator console to a single orientation.

According to an aspect of some example embodiments there is provided a patient circuit kit for a dual-limb patient circuit comprising: an adaptor as described herein above; an external sampler; and tubing connecting the tube connectors on the adaptor to the external sampler.

According to an aspect of some example embodiments there is provided a patient circuit kit for a single-limb patient circuit comprising: an adaptor as described herein above; an external sampler; and tubing connecting a pair of tube connectors on the adaptor to the external sampler and connecting another tube connector to an external exhalation valve.

Optionally, the patient circuit kit further includes an inhalation limb and an exhalation limb.

According to an aspect of some example embodiments there is provided an method for operating a medical ventilator, the method comprising: selecting a patient circuit kit, wherein the patient circuit kit includes an adaptor dedicated to a specific type of patient circuit; plugging the adaptor of the selected patient circuit kit to a console of the medical ventilator; and activating ventilation based on the selected patient circuit kit.

Optionally, the method further includes simultaneously toggling two three-way valves integrated with the ventilator console based on plugging the adaptor to the console.

Optionally, the method further includes simultaneously toggling three three-way valves integrated with the ventilator console based on plugging the adaptor to the console.

Optionally, the adaptor is connected to an external sampler.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 9A, 9B and 9C are a simplified schematic drawing of an exemplary ventilator console and two exemplary patient circuit adaptors, all in accordance with some embodiments of the present disclosure;

Figure 16A:
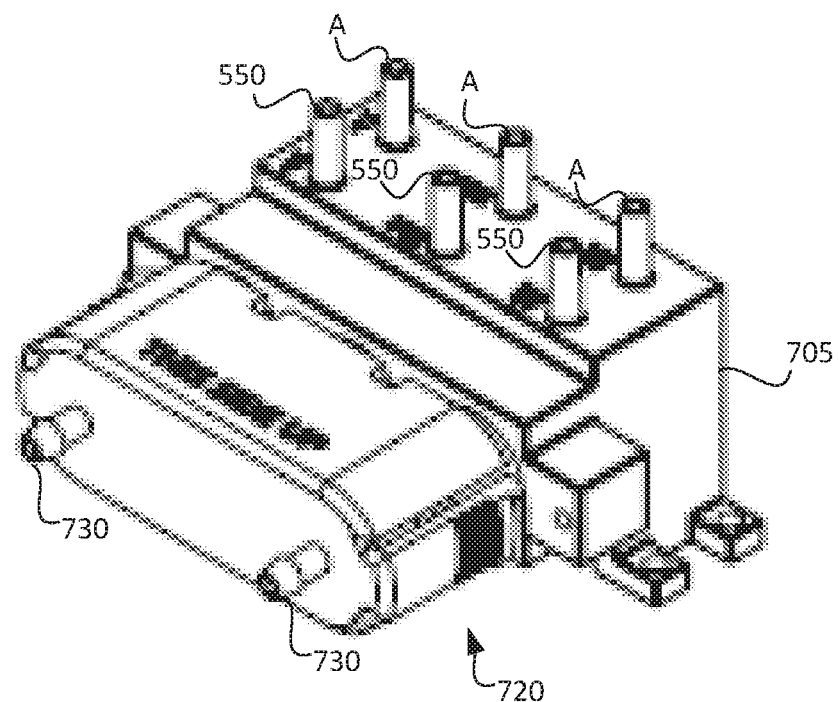
Figure 16B:
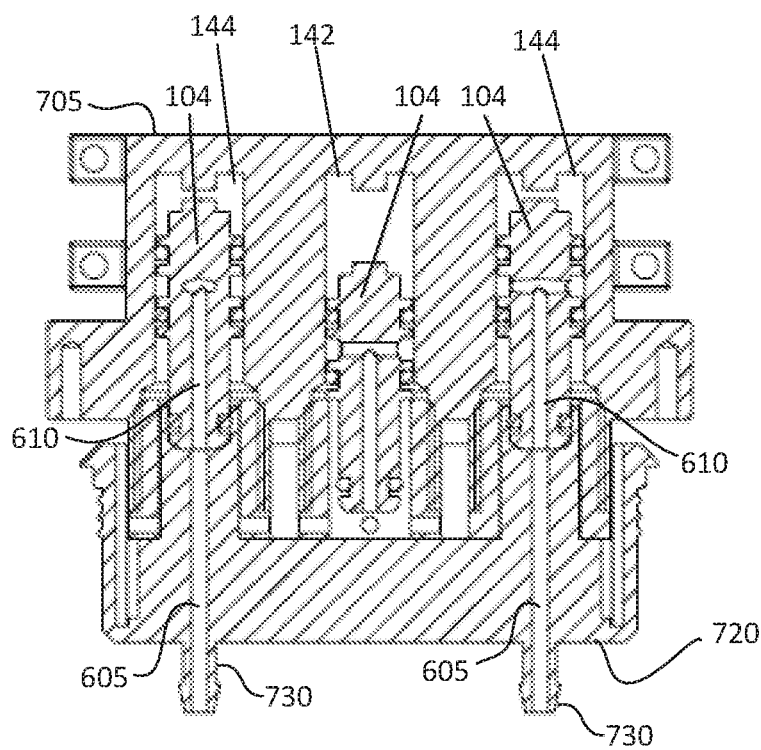
Figure 17A:
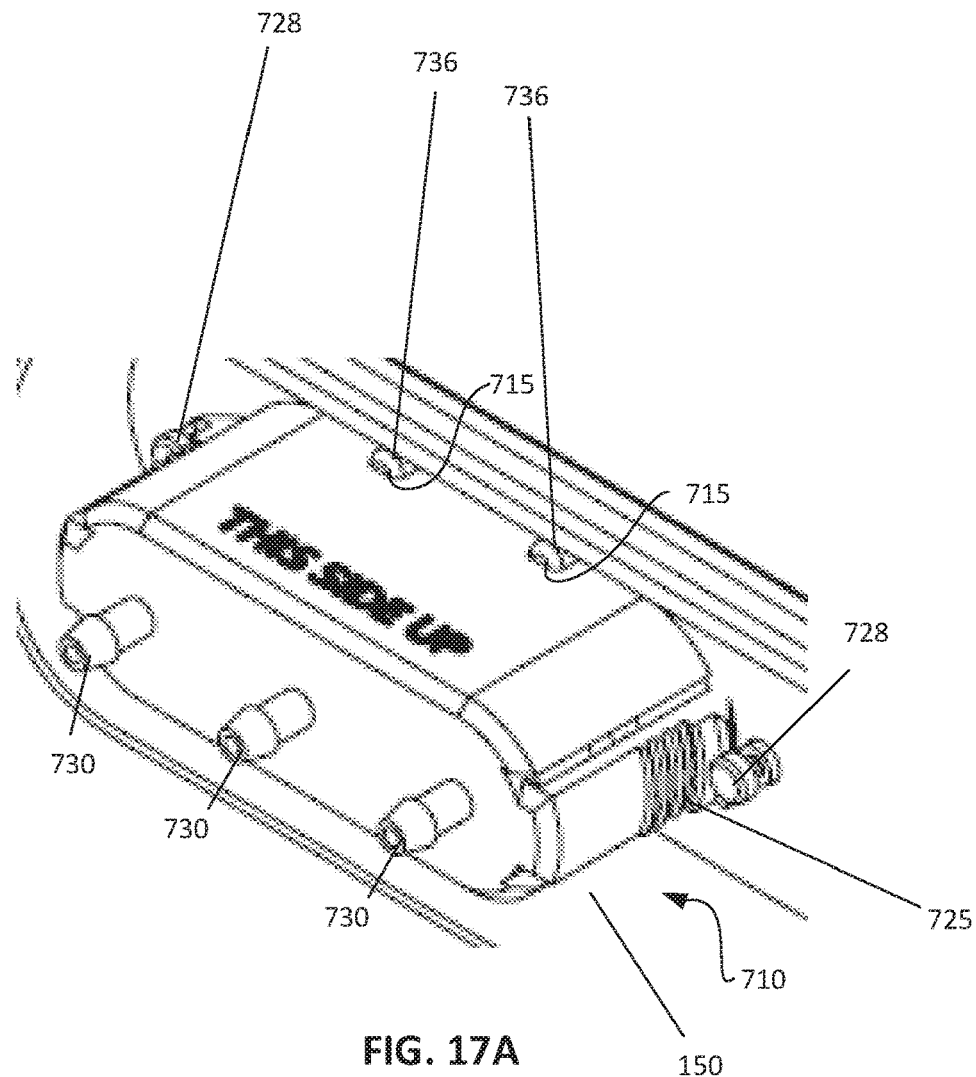
Figure 17B:
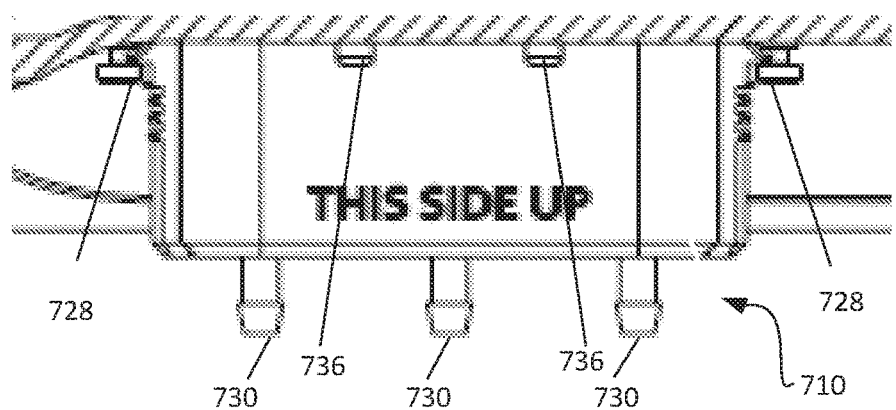
Figure 18A:
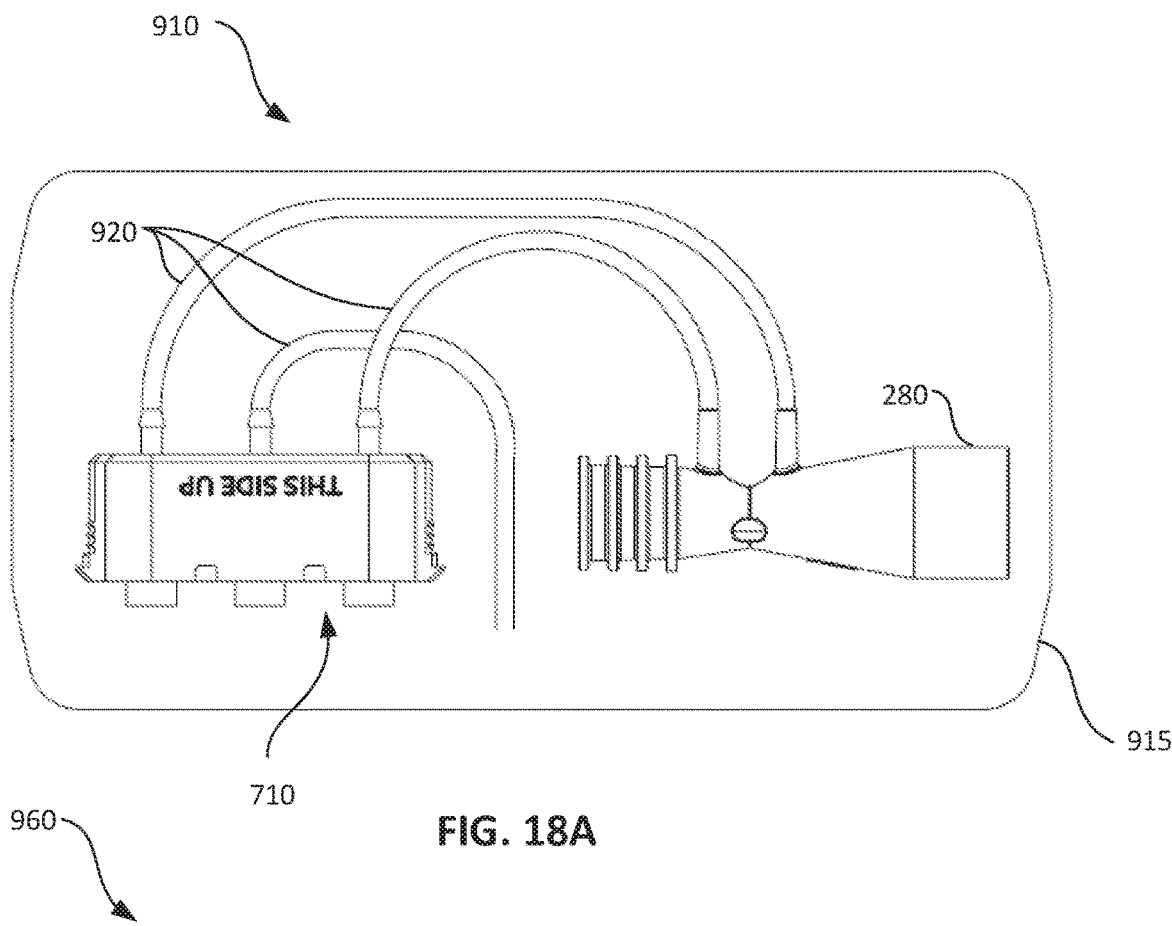
Figure 18B:
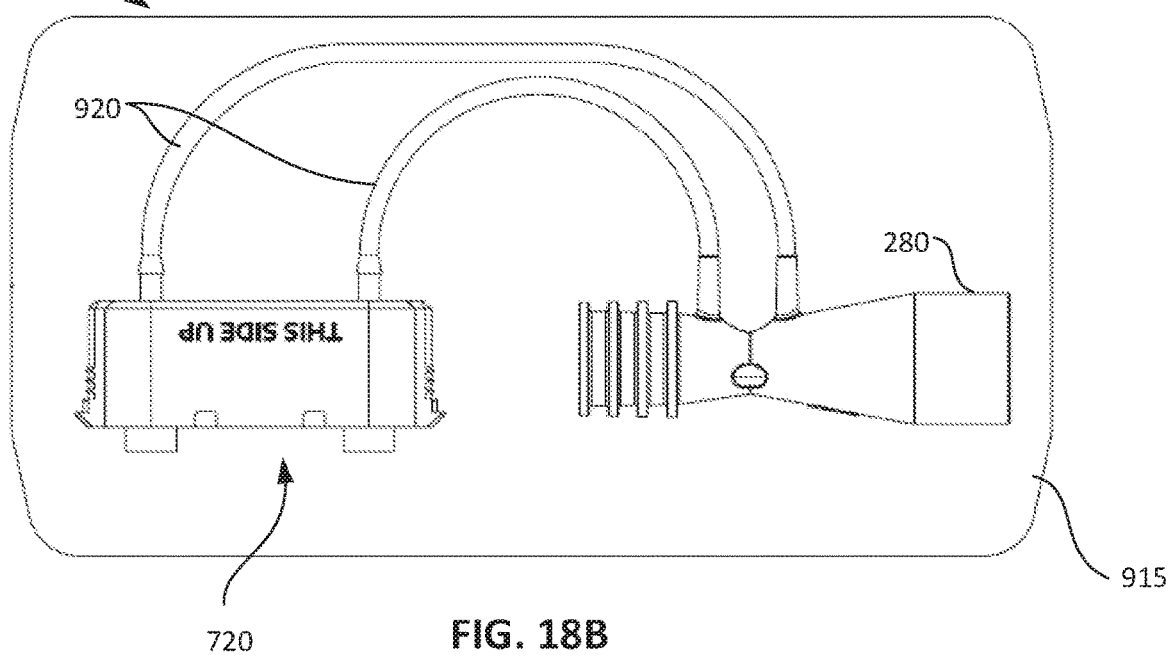
Figure 19A:
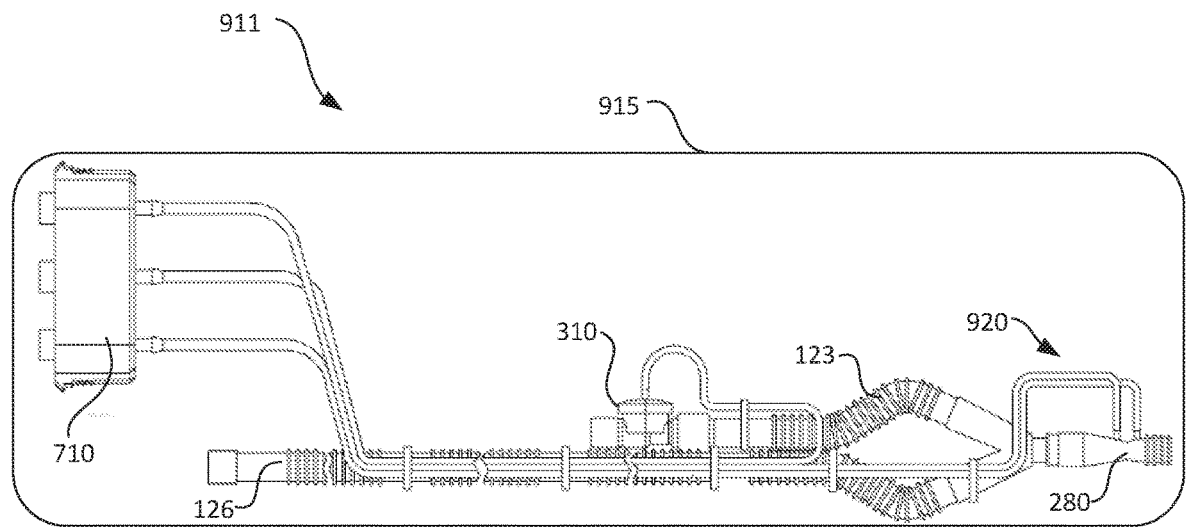
Figure 19B:
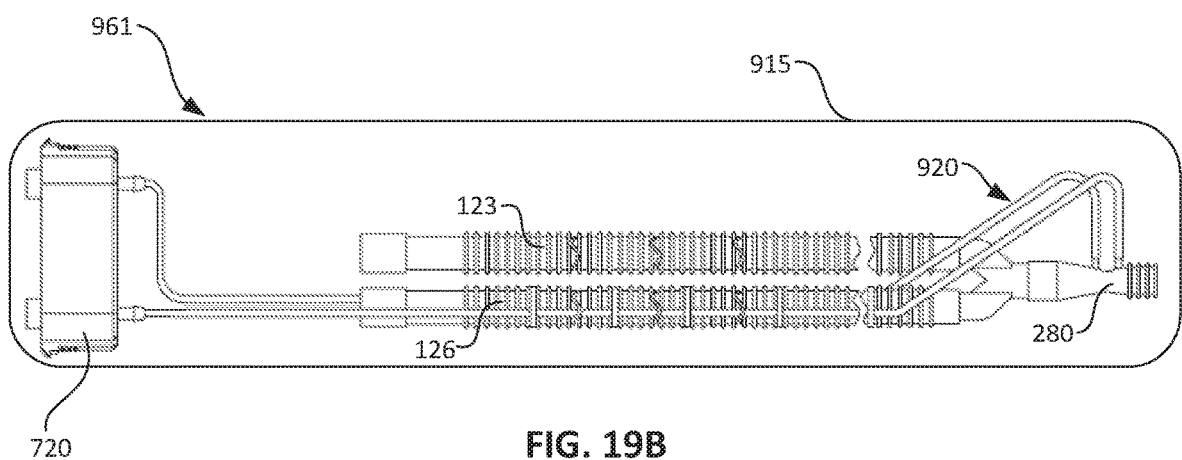
Figure 20:
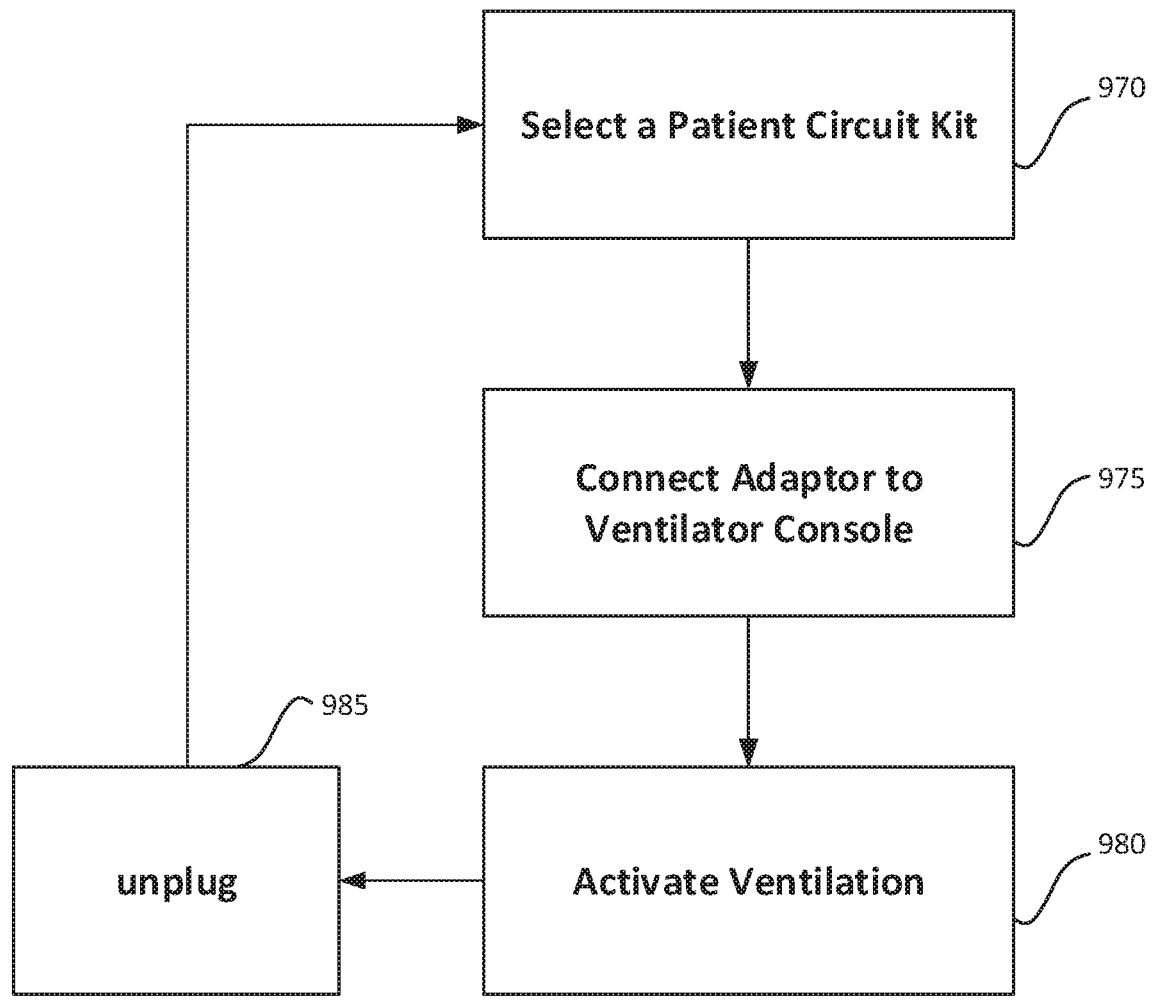

FIGS. 16A and 16B are perspective and cross-sectional views of another exemplary patient circuit adaptor connected to an exemplary valve housing block of a ventilator console in accordance with some embodiments of the present disclosure; and FIGS. 17A and 17B are perspective and top views respectively of an exemplary patient circuit adaptor plugged into an exemplary ventilator console in accordance with some embodiments of the present disclosure;

FIGS. 18A and 18B are a kit for each of a single-limb and dual-limp patient circuit respectively, both in accordance with some embodiments of the present disclosure;

FIGS. 19A and 19B are a kit including a full single-limb and a kit including a full dual-limp patient circuit respectively, both in accordance with some example embodiments; and FIG. 20 is a simplified flow diagram of another exemplary method for switching a patient circuit for a ventilator in accordance with some embodiments of the present disclosure.

DESCRIPTION OF SPECIFIC EMBODIMENTS OF THE INVENTION

The present invention, in some embodiments thereof, relates to a medical ventilator and, more particularly, but not exclusively, to a patient circuit for a medical ventilator.

According to example embodiments, a ventilator console includes a three-way valve installed in each of its two sensing ports and its pneumatic diaphragm pressure port. According to some example embodiments, each of the three-way valves is configured to toggle between internal sensing or control (within the console) and external sensing or control (outside of the console). The sensing ports may provide both pressure and flow sensing based on an internal sampler or an external sampler in the flow path. In some example embodiments, the three-way valve is actuated mechanically based on an operator plugging (or unplugging) a tube of the patient circuit into a port including the three-way valve.

In some example embodiments, the three-way valve is formed with a housing including a common port and a second port, and a piston that slides within the housing against a spring force. The piston may be associated with a third port, an external port through a central drill and a side opening that is formed in the piston. A pair of O-rings positioned on either side of the side opening may guide the piston movement within the housing, seal the valve and confine flow to and from the side opening to a volume between the O-rings.

In a neutral position of the piston, air may freely flow between the common port and the second port while flow between the common port and the side opening may be blocked. When the piston is pushed into the housing, the volume between the O-rings may align with the common port and flow communication may be established between the common port and the side opening while blocking flow between the common port and the second port.

In some example embodiments, plugging a connector of the patient circuit to a port on the console of the ventilator toggles the three-way valve by pushing the piston into the housing and thereby switching a direction of flow from the second port to the third port. Optionally, a bayonet connector locks the connector and piston in place. Optionally, a male part of the bayonet connect is integral to a tube connector that connects an external tube from patient circuit to the third port. As long as the tube connector is plugged into the port in the console, the air flow is between the common port and the third port and external control or/and external measurements are established.

In some example embodiments, disconnecting the connector on the patient circuit, releases the spring in the housing of the valve and pushes the piston back to its neutral position. In the neutral state of the piston, air flow between the common port and the third port is blocked and air flow between the common port and the second port is established. In this configuration, internal control or/and internal measurements are established.

Elements of the three-way valve may be shaped and size to connect to only one of the tube connectors on the patient circuit. In this manner, an operator will not be able to accidently connect a tube of the patient circuit to the wrong port. Connection between tubes of the patient circuit and ports in the console may be based on male to female connecting parts.

According to some example embodiments, a patient circuit adaptor actuates a desired patient circuit based on plugging in the adaptor to the ventilator console with a single plugging motion. Each type of patient circuit may be actuated with a dedicated patient circuit adaptor. For example, one patient circuit adaptor may actuate a dual-limb patient circuit and another patient circuit adaptor may provide a single-limb patient circuit. According to some example embodiments, the different patient circuit adaptors are constructed to selectively toggle valves included in the two sensing ports and the pneumatic diaphragm pressure port of the ventilator console. For both the dual-limb and single-limb patient circuit adaptor, the operator performs the simple plugging motion. According to some example embodiments, each of the valves included in the two sensing ports and the pneumatic diaphragm pressure port are three-way valve that toggle between establishing flow or pressure communication to the console sampler and establishing flow or pressure communication to the at least one external control port, wherein the toggling is actuated based on plugging or unplugging the patient circuit adaptor.

In some example embodiments, each adaptor may include tube connectors on which tubes leading to an external sampler and/or an external exhalation valve as needed. Optionally, the adaptors are preinstalled with the tubes so that the operator does not need to decide which tube is to be connected to each of the tube connectors on the adaptor. For example, a patient circuit adaptor for a dual-limb circuit may include two tube connectors that are configured to connect to an external sampler and a patient circuit adaptor for a single-limb circuit may include three tube connectors that are configured to be connected to an external sampler and an external exhalation valve.

According to some example embodiments, the patient circuit adaptor includes a safety mechanism to ensure that the adaptor is plugged into the ventilator console in the correct orientation. While the patient circuit adaptor is not connected to ventilator console, ventilation may be operated by default with internal pressure and flow measurements and internal exhalation valve control.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Figure 1A:
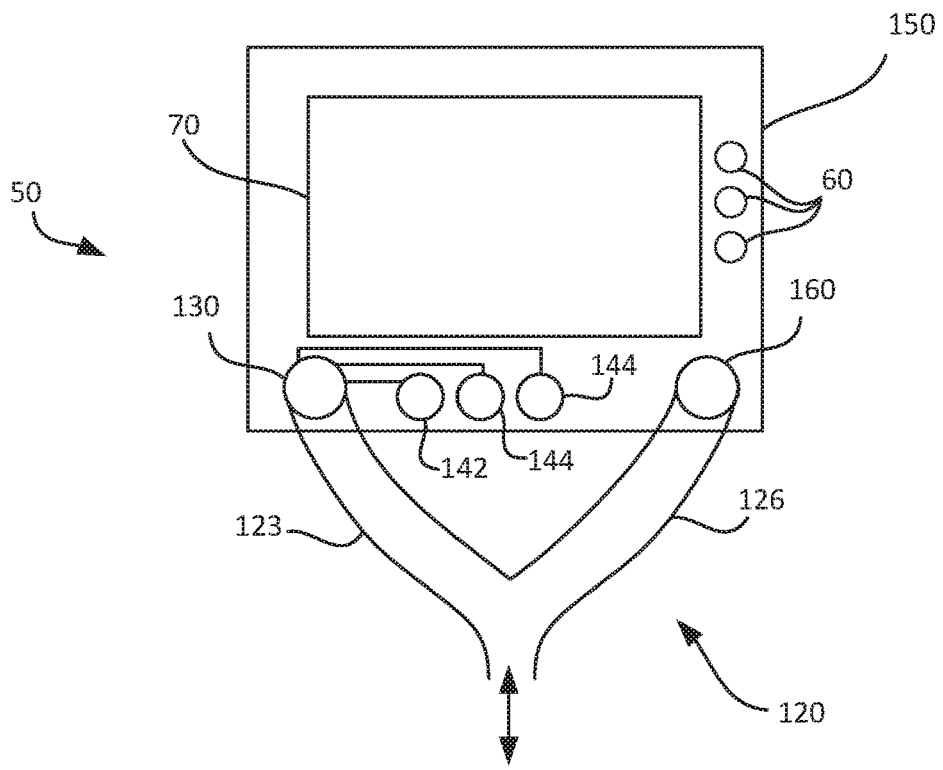
FIG. 1A is a simplified schematic drawing of an exemplary patient circuit including internal pressure and flow measurements and internal exhalation valve control in accordance with some embodiments of the present disclosure.
Figure 1B:
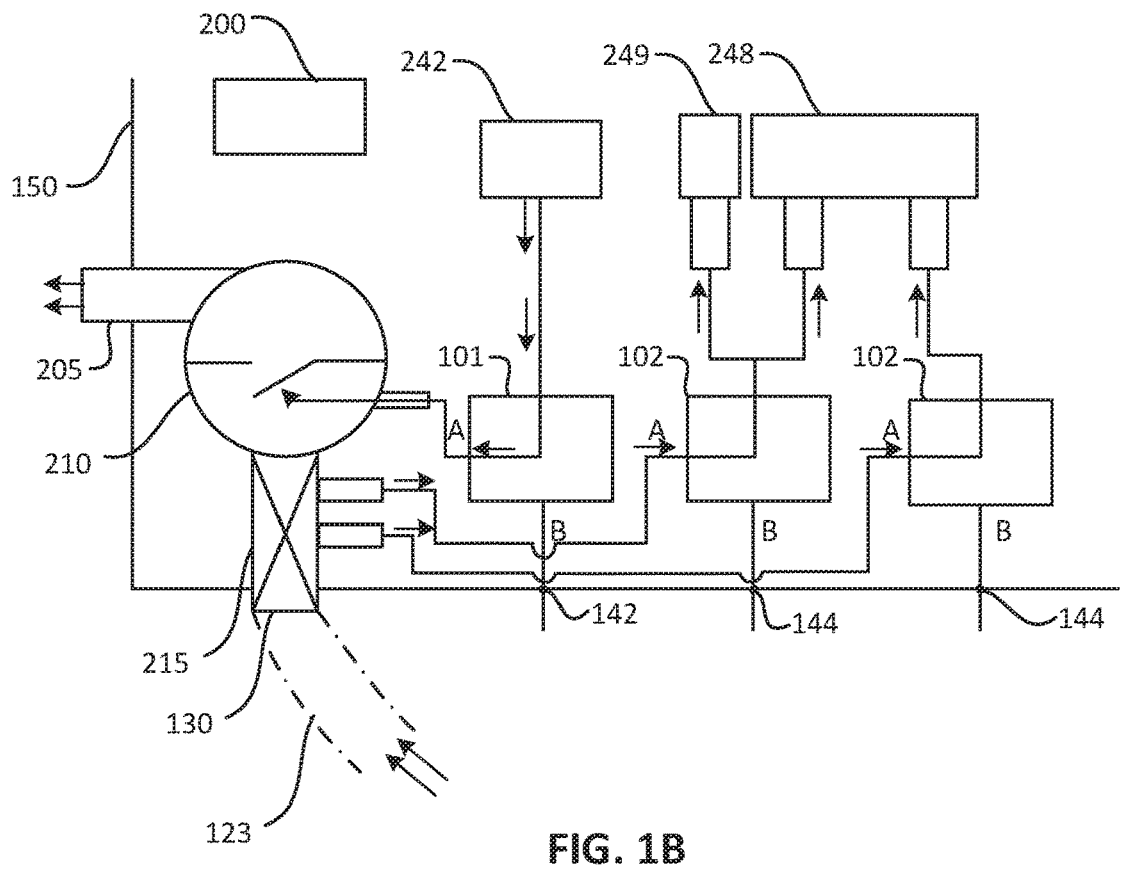
FIG. 1B is an exemplary air pathway block diagram including internal pressure and flow measurements and internal exhalation valve control in accordance with some embodiments of the present disclosure.

Reference is now made to FIGS. 1A and 1B showing respectively a simplified schematic drawing of an exemplary patient circuit and an exemplary air pathway block diagram for operating a ventilator with internal pressure and flow measurements and internal exhalation valve control in accordance with some embodiments of the present disclosure. A console 150 of a medical ventilator 50 may typically include a plurality of ports via which a patient circuit 120 may deliver and control breathing of a patient. Typical ports available on console 150 include an inhalation port 160 via which gas is delivered to the patient, an exhalation port 130 via which gas that is exhaled from patient may be received, a pneumatic diaphragm pressure port 142 via which an external exhalation valve may be fluidly connected and two ports 144 for one or more of pressure and flow sensing via which an external sampler may be connected. Console 150 may include a display 70 and one or more control buttons or dials 60 to turn ON/OFF and/or control operation of medical ventilator 50. Typically, medical ventilator 50 includes a controller 200 configured to control operation of the ventilator. Medical ventilator 50 may be setup to control exhalation based on an exhalation valve 210 included on console 150 or may be setup to control exhalation based on an exhalation valve connected to patient circuit 120 (external from console 150 and more proximal to the patient). Similarly, medical ventilator 50 may be set up to sense pressure or flow velocity based on measurements from a sampler 215 included in console 150 or may be setup to sense pressure or flow velocity based on measurements from a sampler included on patient circuit 120 (external from console 150 and more proximal to the patient).

According to some example embodiments, pneumatic diaphragm pressure port 142 includes a three-way valve 101 that toggles between directing pressure or flow from a pressurized air source 242 through a port A to internal exhalation valve 210 for internal exhalation control (within console 150) and directing pressure or flow from pressurized air source 242 externally through a port B for external exhalation control (external from console 150). According to some example embodiments, each of ports 144 likewise include a three-way valve 102 that toggles between receiving input (flow or pressure input) from sampler 215 through a port A and receiving input (flow or pressure input) externally through a port B. The received input may be directed to delta pressure sensor 248 and pressure sensor 249 for pressure and flow sensing respectively.

According to embodiments of the present disclosure, each of the three-way valves are toggled based on plugging and unplugging a tube connector to its associated port. Plugging and unplugging may be based on manual manipulation by the operator or may be based on an electro mechanical or pneumatic element controlled remotely with a control system.

As shown in FIGS. 1A and 1B, while no tube connector is plugged into port 142, a three-way valve 101 in ventilator 50 diverts pressure or flow from pressurized air source 242 via a port A of three-way valve 101 to an internal exhalation valve 210. In this configuration, exhalation from a patient flows through exhalation limb 123 through exhalation valve 210 within console 150 and may be expelled through an exhaust 205 in console 150. As shown in FIGS. 1A and 1B, while no tube connector is plugged into ports 144, each of three-way valves 102 may direct pressure or flow from respective points in an internal sampler 215 included in medical ventilator 50 via port A of the three-way valves 102 to delta pressure sensor 248 and to pressure sensor 249. Flow through inhalation limb 126 is not shown in the air pathway block diagram for simplification purposes. According to some example embodiments, three-way valve 101 and three-way valves 102 are configured to communicate air pressure and flow internally in its default or neutral position, e.g. while no force is applied on the three-way valve.

Figure 2A:
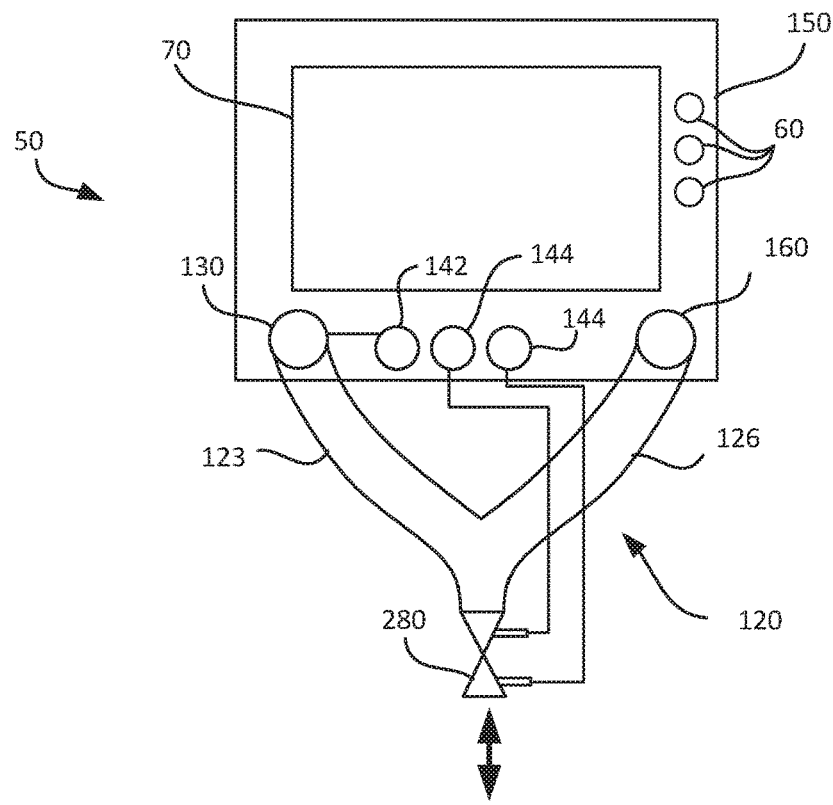
FIG. 2A is a simplified schematic drawing of an exemplary patient circuit including external pressure and flow measurements and internal exhalation valve control in accordance with some embodiments of the present disclosure.
Figure 2B:
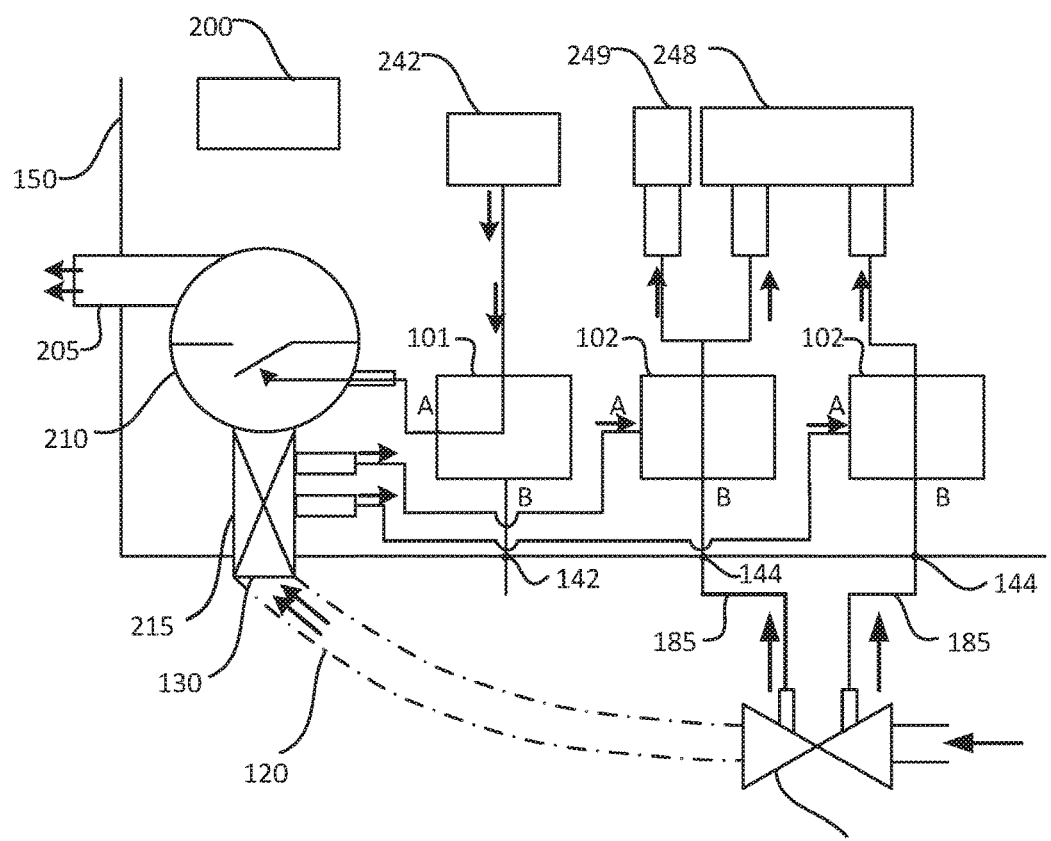
FIG. 2B is an exemplary air pathway block diagram including external pressure and flow measurements and internal exhalation valve control in accordance with some embodiments of the present disclosure.

Reference is now made to FIGS. 2A and 2B showing respectively a simplified schematic drawing for an exemplary patient circuit and an exemplary air pathway block diagram for external pressure and flow measurements and internal exhalation valve control in accordance with some embodiments of the present disclosure. In some example embodiments, an operator may actuate sensing based on connecting tubes 185 from an external sampler on patient circuit 120 to ports 144 on console 150. According to embodiments of the present disclosure, the act of plugging tube connectors of tubes 185 into ports 144 actuates toggling of three-way valves 102 for external sensing through port B of the three-way valve. In this configuration, delta pressure sensor 248 and pressure sensor 249 receive flow and pressure samples directly from patient circuit 120 via external sampler 280. According to embodiments of the present disclosure, external sensing may be actuated at the start of ventilation and may also be actuated over a course of ventilation without interrupting the ventilation.

Figure 3A:
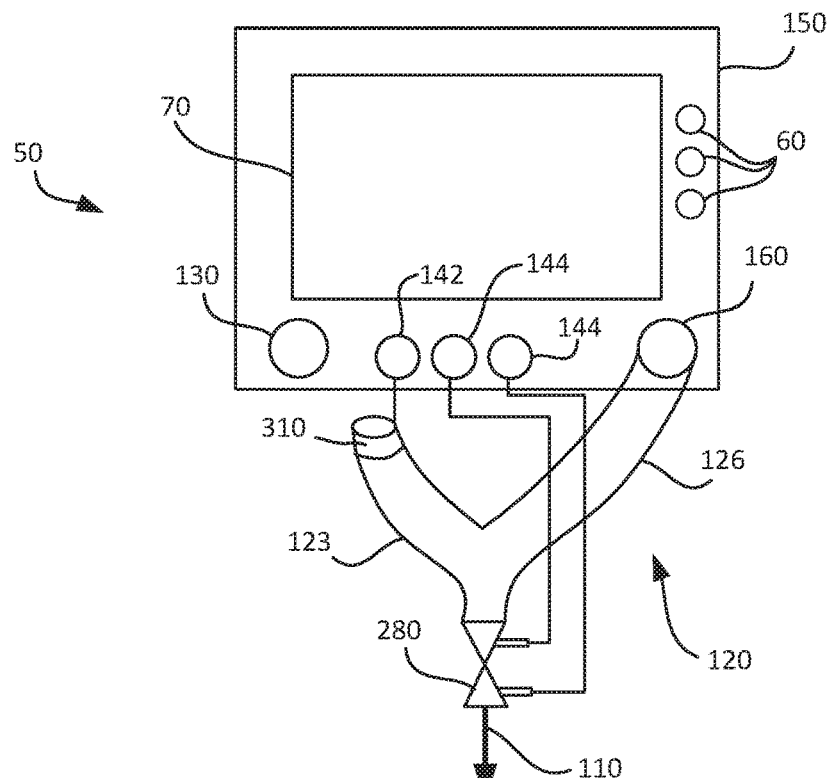
FIG. 3A is a simplified schematic drawing of an exemplary patient circuit including external pressure and flow measurements and external exhalation valve control in accordance with some embodiments of the present disclosure.
Figure 3B:
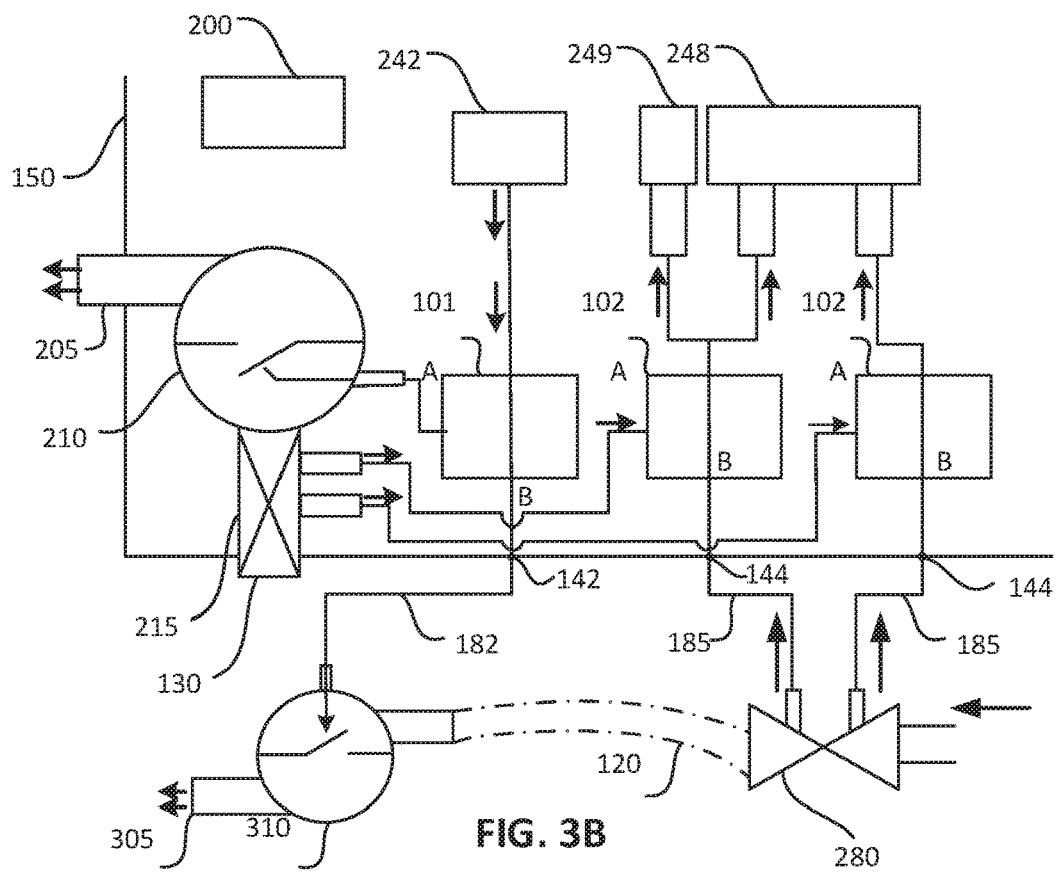
FIG. 3B is an exemplary air pathway block diagram including external pressure and flow measurements and external exhalation valve control in accordance with some embodiments of the present disclosure.

Reference is now made to FIG. 3A and FIG. 3B showing respectively a simplified schematic drawing of an exemplary patient circuit and an exemplary air pathway block diagram for external pressure and flow measurements and external exhalation valve control in accordance with some embodiments of the present disclosure. In some example embodiments, an operator may actuate external exhalation control based on connecting tube 182 from an external exhalation valve 310 on patient circuit 120 to ports 142 on console 150. According to embodiments of the present disclosure, the act of plugging a tube connector of tube 182 into port 142 actuates toggling of three-way valve 101 for external control through port B of three-way valve 101. In this configuration, pressure or flow from pressurized air source 242 is directed to external exhalation valve 310 and gas exhaled is exhausted through a port 305 in patient circuit 120. According to embodiments of the present disclosure, external exhalation control may be actuated at the start of ventilation and may also be actuated of the course of ventilation without pausing ventilation. Furthermore, toggling between external and internal exhalation control may be actuated independently from toggling between external and internal sensing. For example, an operator may choose to sample pressure and flow internally and control exhalation externally based on connecting tube 182 (FIG. 3B) and disconnecting tubes 185 (FIG. 2B).

Figure 4:
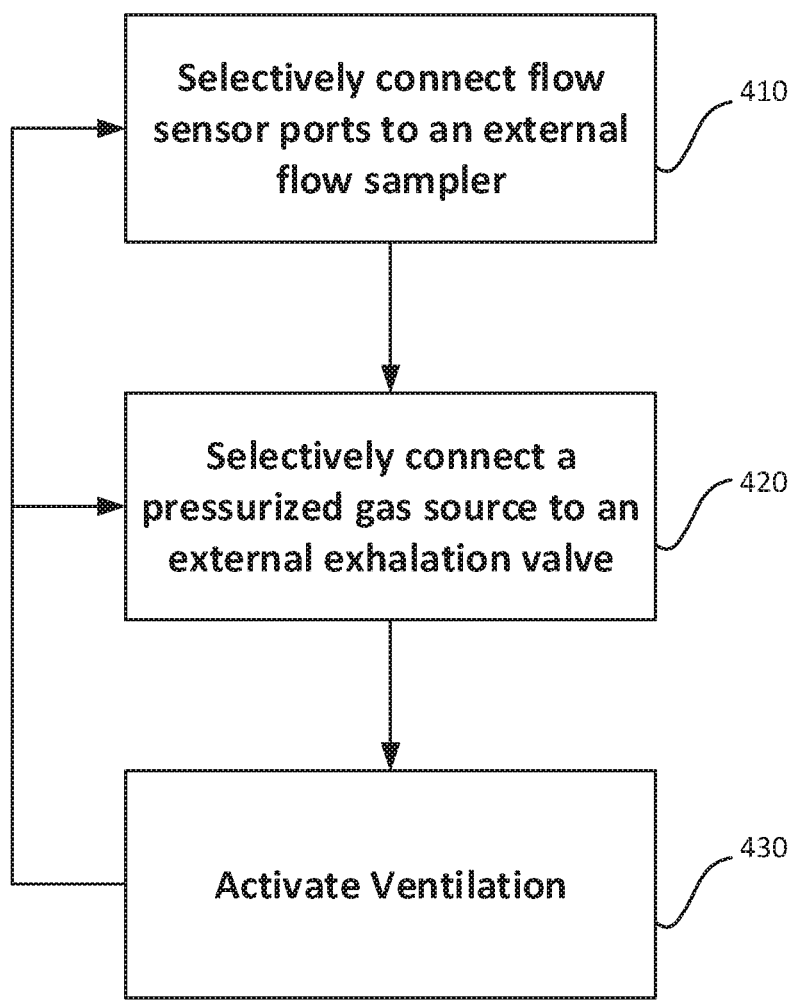
FIG. 4 is a simplified flow diagram of an exemplary method for switching a patient circuit for a ventilator in accordance with some embodiments of the present disclosure.

Reference is now made to FIG. 4 showing a simplified flow diagram of an exemplary method for switching a patient circuit for a ventilator in accordance with some embodiments of the present disclosure. In some example embodiments, an operator may selectively fluidly connect an external sampler 280 to sensor ports 144 by selectively plugging in a pair of tube connectors into flow sensing ports 144 (block 410). In some example embodiments, an operator may selectively fluidly connect an external exhaust valve 310 to pneumatic diaphragm pressure port 142 by selectively plugging in a tube connector into pneumatic diaphragm pressure port 142 (block 420). A user may then activate the ventilation (block 430) to obtain ventilation based on the control and sensing as selected. Over the course of ventilation, the operator may alter the setting by toggling connection from an external sampler 280 to an internal sampler 215. Toggling connection from an external sampler 280 to an internal sampler 215 may be based on plugging/unplugging a tube connector that connects external sampler 280 to ports 144. An operator may also alter the setting by toggling connection from an external exhalation valve 310 to an internal exhalation valve over the course of ventilation. Toggling connection from an external exhalation valve 310 to an internal exhalation valve 210 may be based on plugging/unplugging a tube connector that connects external exhalation valve 310 pneumatic diaphragm pressure port 142. Toggling may be performed just based on plugging or unplugging a tube connector to the patient circuit.

Figure 5A:
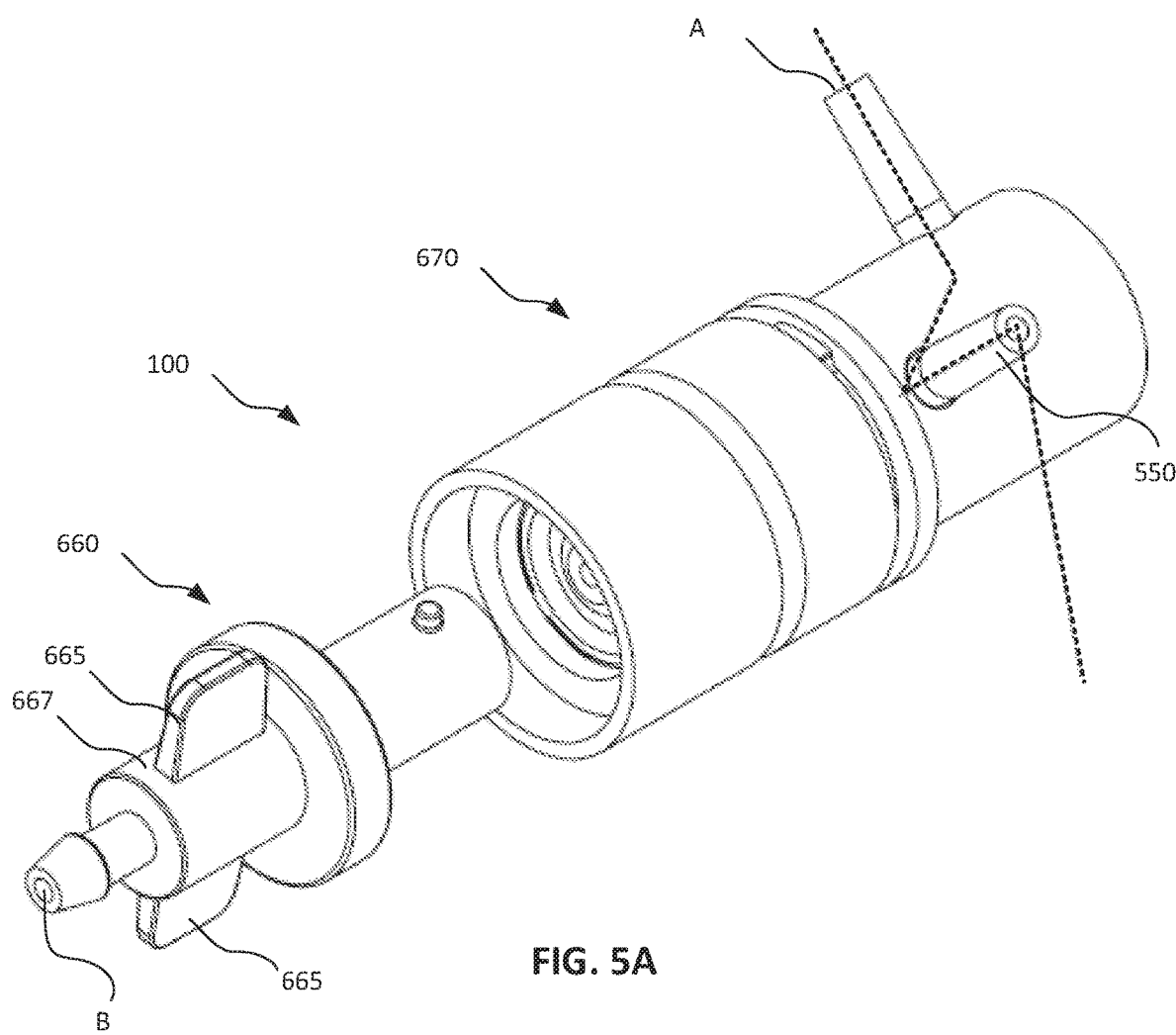
FIGS. 5A and 5B are perspective view of an exemplary three-way valve for a ventilator in a respective unplugged and plugged configuration in accordance with some embodiments of the present disclosure.
Figure 5B:
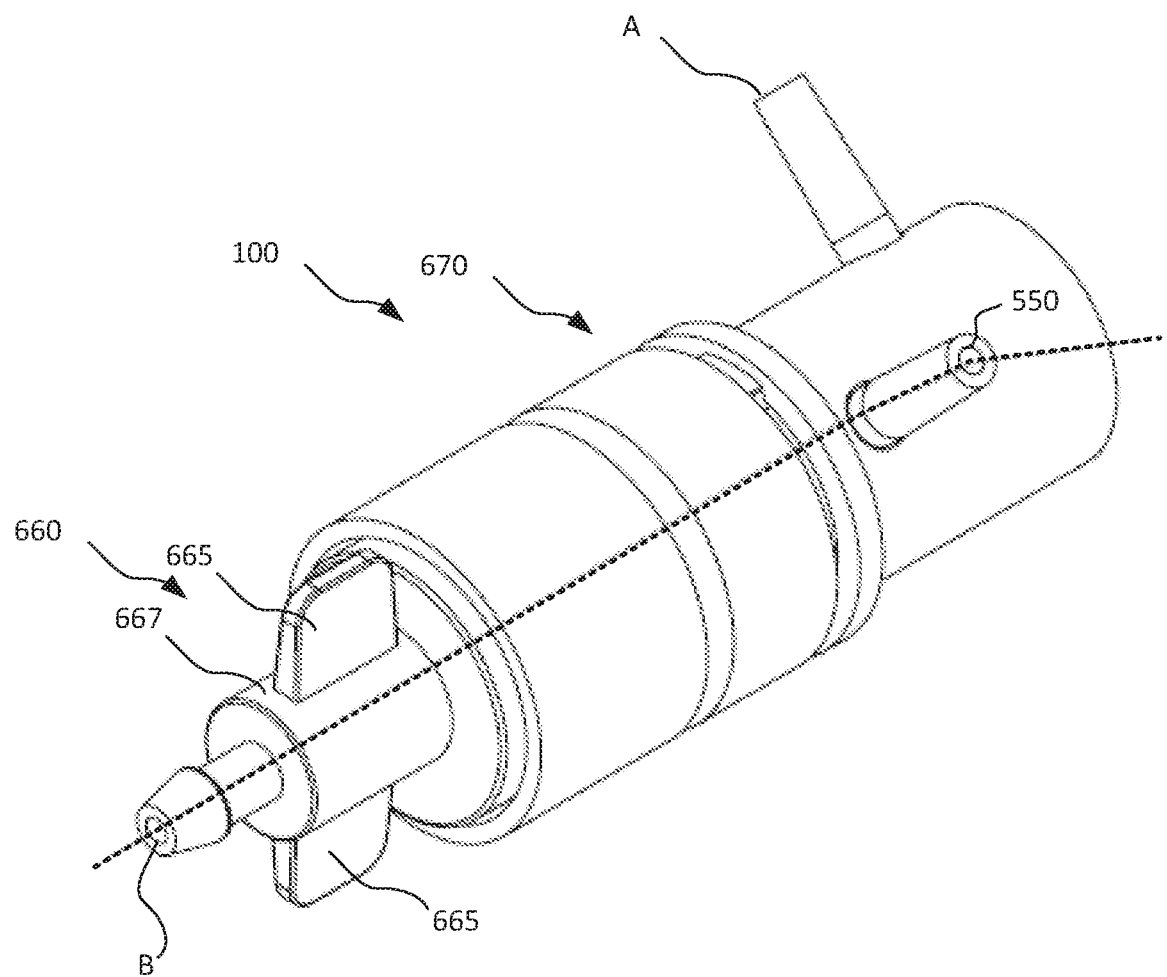

Reference is now made to FIGS. 5A and 5B showing perspective view of an exemplary three-way valve for a ventilator in a respective unplugged and plugged configuration in accordance with some embodiments of the present disclosure. According to some embodiments of the present disclosure valve 101 and each of valves 102 include a base portion 670 including a common port 550 and port A that is installed in medical ventilator 50 and a tube connector 660 that is connected to an end of a tube extending from patient circuit 120 (FIG. 5A). In some example embodiments, while tube connector 660 is disconnected from base portion 670 in console 150, three-way valve diverts pressure or flow between a common port 550 and port A. Common port 550 may connect to pressurized air source 242 in three-way valve 101 and may connect to delta pressure sensor 248 and/or pressure sensor 249 in three-way valve 102. Port A may be connected to internal exhalation valve 210 in three-way valve 101 and to an internal sampler 215 in three-way valve 102.

Referring now to FIG. 5B, based on plugging tube connector 660 into base portion 670, pressure or flow diverted between common port 550 and port A is blocked and instead pressure or flow is diverted between common port 550 and port B. A user may for example hold cylindrical portion 667 to insert tube connector 660 into base portion 670 and may use tabs 665 to lock in tube connector 660 by turning tube connector 660 into base portion 670.

Figure 6:
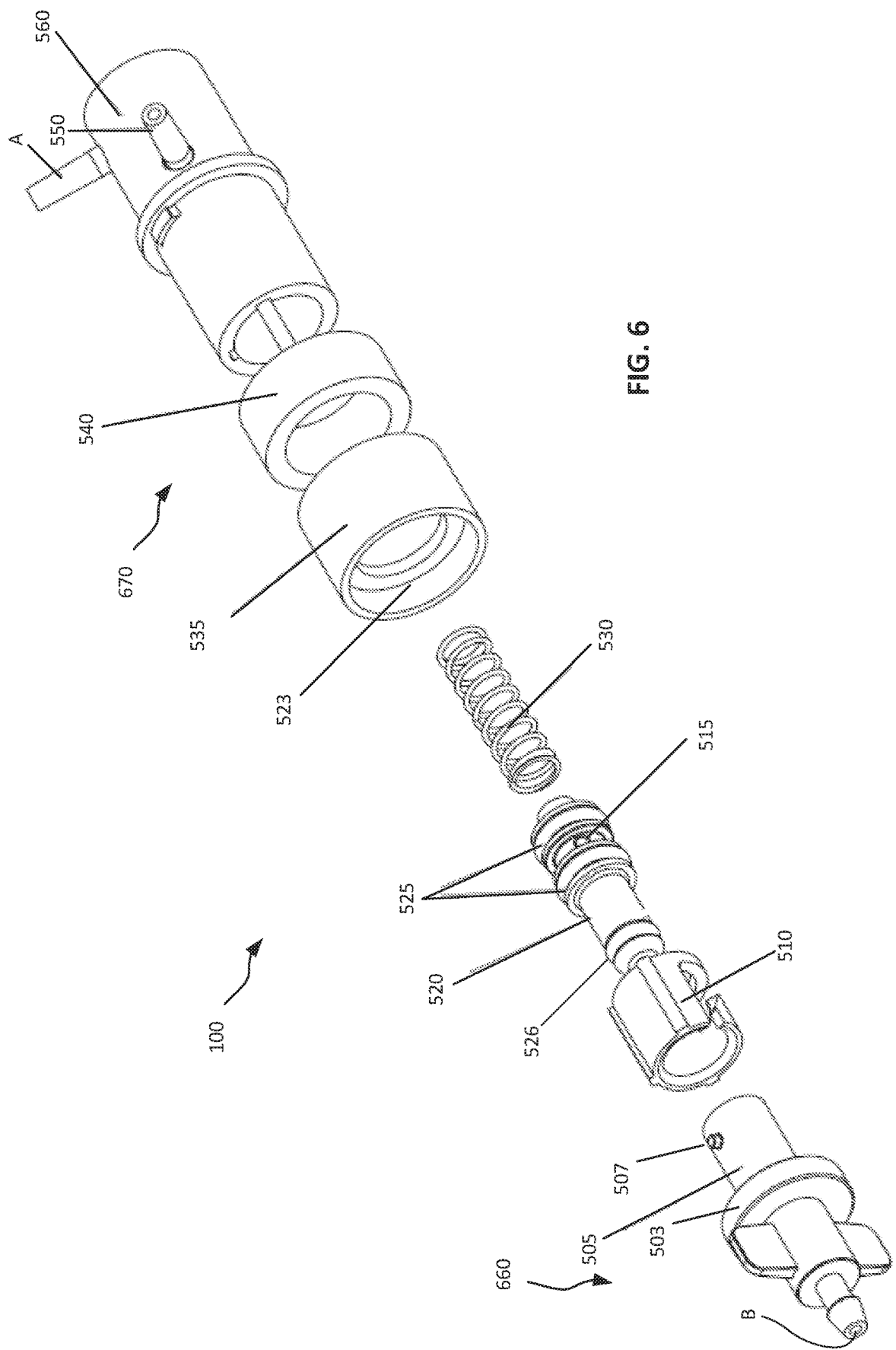
FIG. 6 is an exemplary exploded view of a three-way valve for a ventilator in accordance with some embodiments of the present disclosure.

Reference is now made to FIG. 6 showing an exemplary exploded view of a three-way valve for a ventilator in accordance with some embodiments of the present disclosure. In some example embodiments, three-way valve 100 includes a housing 560 formed with common port 550 and port A, a spring element 530 housed in housing 560, a piston 520 that moves within along housing 560 against spring element 530 and a bayonet connector configured to lock tube connector 660 to base portion 670. Bayonet connector may include a male portion 505 with pin 507 that fits into a bayonet slot 510. Bayonet slot may be secured in a lock housing 535 to housing 560. Nut 540 secures housing 560 against a wall of console 150. According to some example embodiments, Bayonet connector may be shaped and sized differently for each of three-way valves 101 and 102 so that an operator can only fit tube connector 660 into its dedicated port on console 150. Lock housing 535 may include a recess 523 for receiving a flange 503 of tube connector 660. According to some example embodiments, flange 503 and corresponding recess 523 is sized differently for each of three-way valves 101 and 102 so that an operator cannot fit tube connector 660 into the wrong port. According to some example embodiments, each of flange 503, pin 507, bayonet slot 510, recess 523 are sized differently for each of the three-way valves 100 installed in medical ventilator 50. In some example embodiments, the combination of these different sizes makes it possible to create a dedicated connection between each connector 660 and its matching base portion 670 and prevent connection of connector 660 into the wrong port on the console.

In some example embodiments, piston 520 includes a central drill connected to a side opening 515. Optionally, a pair of O-rings 525 selectively isolates pressure and flow from side opening 515 to common port 550 and port B. Alternatively, only the one O-ring between side opening and common port 550 may be needed. In some example embodiments, pressure or flow communication between common port 550, through side opening 515, through central drill and port B is established based on piston 520 being pushed into housing 560 until O-rings 525 are positioned on either side of common port 550 and thereby side opening 515 is aligned with common port 550.

Figure 7A:
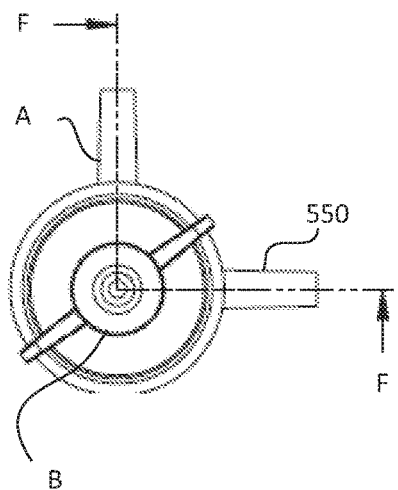
FIGS. 7A and 7B are front and cross-sectional views of an exemplary three-way valve for a ventilator in an unplugged configuration in accordance with some embodiments of the present disclosure.
Figure 7B:
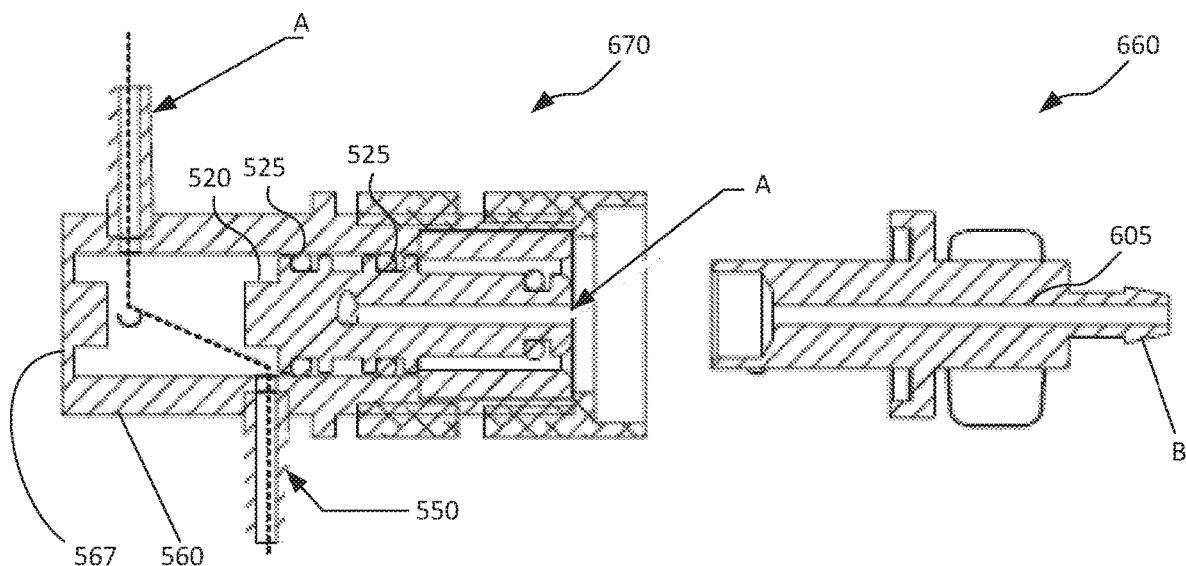

Reference is now made to FIGS. 7A and 7B showing front and cross-sectional views of an exemplary three-way valve for a ventilator in an unplugged configuration in accordance with some embodiments of the present disclosure. While tube connector 660 is disengaged from base portion 670, piston 525 is displaced from back wall 567 of housing 560 and diverts the pressure or flow to connect between common port 550 and port A. O-rings 525 block pressure or flow from a side opening in piston 525 and both common port 550 and port A on housing 560. Spring 530 is not shown in this cross section for simplification purposes.

Figure 8A:
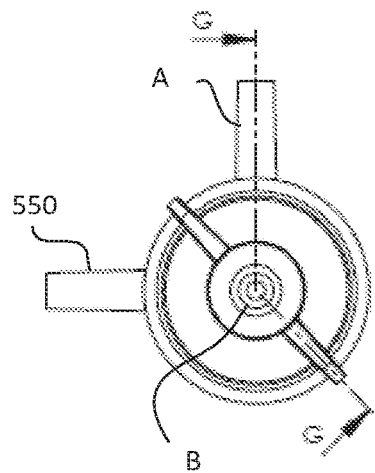
FIGS. 8A and 8B are front and cross-sectional views of an exemplary three-way valve for a ventilator in plugged configuration in accordance with some embodiments of the present disclosure.
Figure 8B:
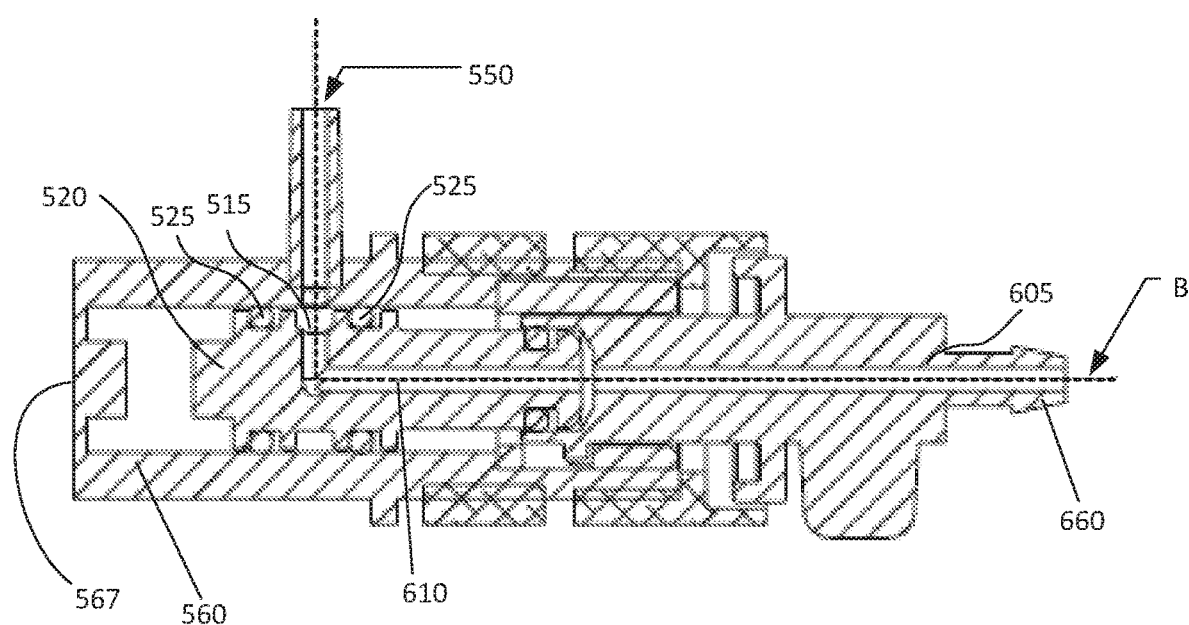

Reference is now made to FIGS. 8A and 8B showing front and cross-sectional views of an exemplary three-way valve for a ventilator in plugged configuration in accordance with some embodiments of the present disclosure. In some example embodiments, plugging in tube connector 660 to base portion 670 pushes piston 520 toward back wall 567 of housing 560 until side opening 515 in piston 520 establishes pressure and flow communication with common port 550. In this position, O-rings 525 are positioned on either side of common port 550 and fluid may flow between common port 550 and port B. Port B extends through central drill 610 of piston 520 connects through central drill 605 of tube connector 660. Piston 520 may be held into place against a spring force with a bayonet connector and may be pushed forward with spring force when the bayonet connector is released. In this manner, the pneumatic sensing and control system may switch based on a "plug and play" mechanism placed at a front face of the console.

Figure 10A:
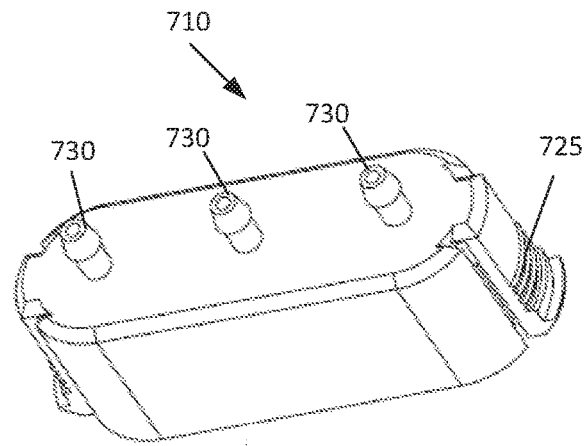
FIGS. 10A and 10B are perspective front-bottom and back-top views respectively of a single-limb patient circuit adaptor in accordance with some embodiments of the present invention.
Figure 10B:
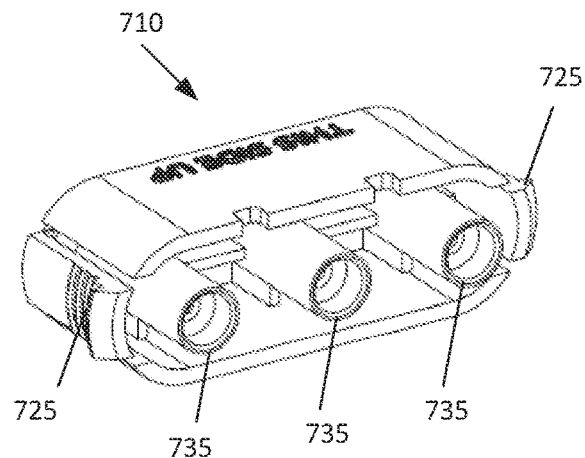
Figure 11A:
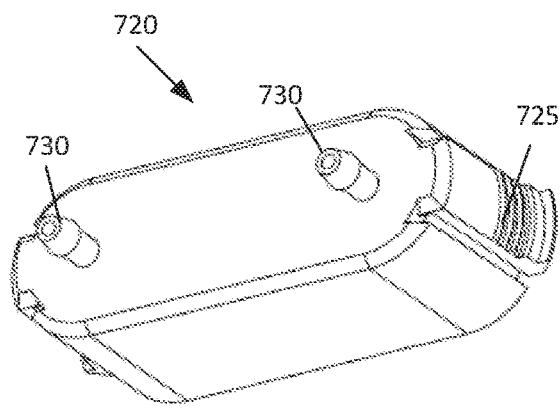
FIGS. 11A and 11B are perspective front-bottom and back-top views respectively of a dual-limb patient circuit adaptor in accordance with some embodiments of the present disclosure.
Figure 11B:
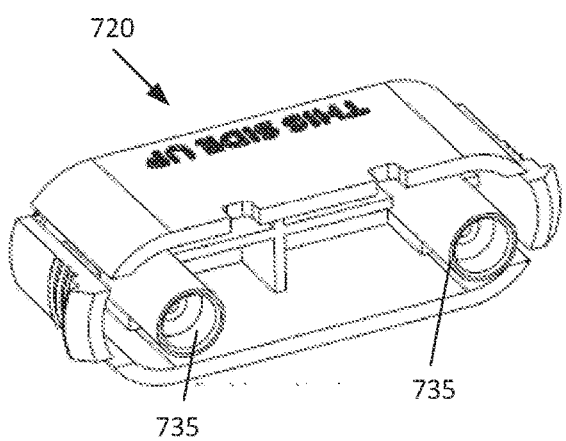

Reference is now made to FIGS. 9A, 9B and 9C showing a simplified schematic drawing of an exemplary ventilator console and two exemplary patient circuit adaptors, to FIGS. 10A and 10B showing perspective front-bottom and back-top views respectively of a single-limb patient circuit adaptor, and to FIGS. 11A and 11B showing perspective front-bottom and back-top views respectively of a dual-limb patient circuit adaptor all in accordance with some embodiments of the present disclosure. According to some example embodiments, a ventilator 51 includes pneumatic diaphragm pressure port 142 via which an external exhalation valve may be fluidly connected and two ports 144 for pressure and/or flow sensing. A female connector or bolt 740 may be connected to each of ports 142 and 144. Optionally, female connector 740 is in the form of an annular ring that may protrude from a surface of ventilator console 151 and may have a depth through which a corresponding male connector 735 may be received. Male connectors 735 may be integrated into an adaptor, e.g. an adaptor 710 with three male connectors 735 or an adaptor 720 with two male connectors 735. Male connector may include an internal drill through which fluid communication may be established between tube connector 730 and a corresponding female connector 740 via male connector 735.

According to some example embodiments, a single-limb adaptor 710 includes three tube connectors 730 on an external face and three corresponding male connectors 735 inside the adaptor or on an opposite face (FIG. 10B). Based on connecting single-limb adaptor 710 to ventilator console 151, fluid communication may be established with each of ports 142 and 144 to provide a single-limb patient circuit. According to some example embodiments, a dual-limp adaptor 720 includes two tube connectors 730 on an external face and two corresponding male connectors 735 inside the adaptor (FIG. 11B). Based on connecting dual-limb adaptor 720 to ventilator console 51, fluid communication may be established with each of ports 144 to provide a dual-limb patient circuit. External connection with pneumatic diaphragm pressure port 142 is excluded for a dual-limb configuration.

According to some example embodiments, each of adaptors 710 and 720 include a housing 724 with clips 725 that may be pressed inwards with pins or notches 728 on ventilator console 51 when mounted thereon to secure the adaptors in place. Correct orientation of the adaptor on ventilator console 51 may be defined with recesses 715 on an upper surface of the adaptors 710 and 720 that match in size and location with notches or pins 736 on ventilator console 51.

Adaptors 710 and 720 may be formed from a polymer material and may be disposable. Optionally, each of adaptors 710 and 720 is packaged with tubes connected to tube connectors 730 and with an external sampler.

Figure 12:
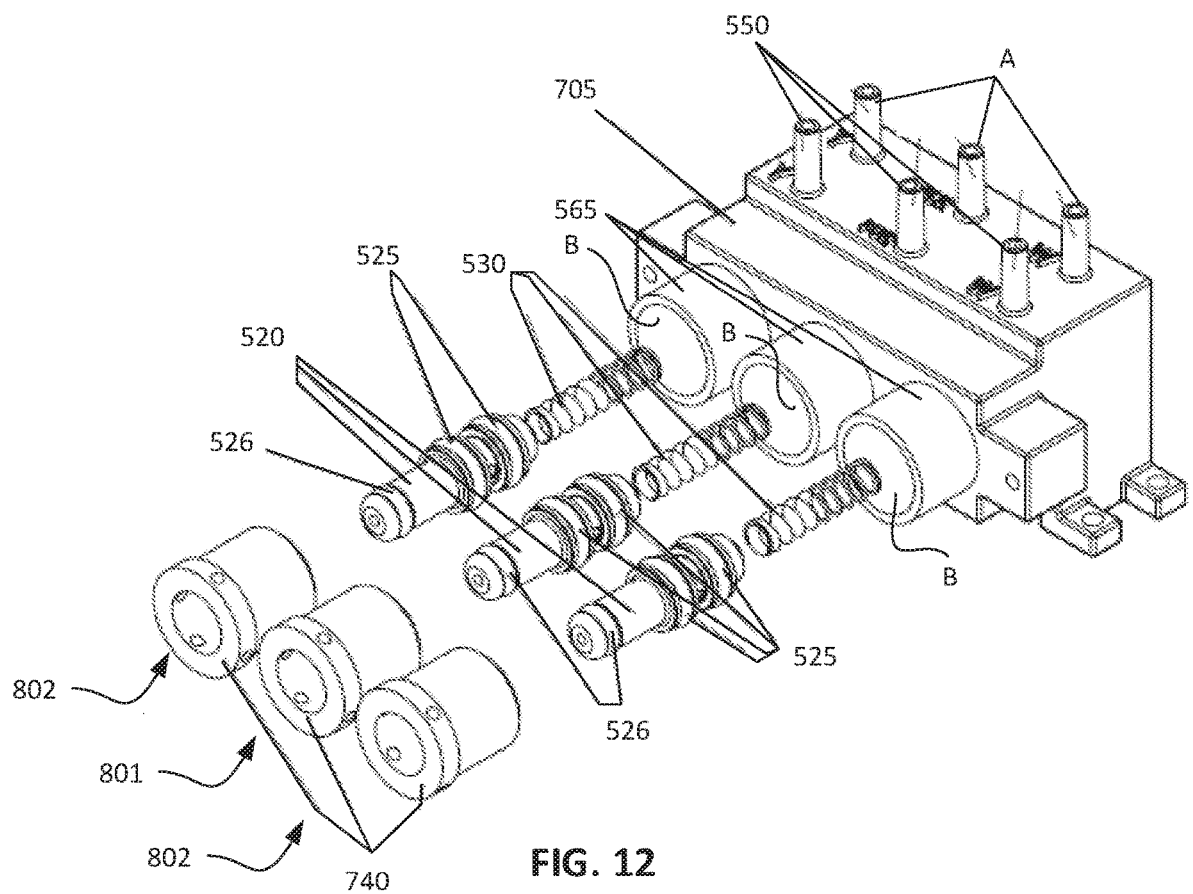
FIG. 12 is an exploded view of an exemplary valve housing block of a ventilator console in accordance with some embodiments of the present disclosure.

Reference is now made to FIG. 12 showing an exploded view of an exemplary valve housing block of a ventilator console in accordance with some embodiments of the present disclosure. According to some example embodiments, valve housing block 705 includes three valve housings 565 each defining a bore with a dedicated common port 550, a port A and a port B. Each valve housing 565 is installed with a three-way valve 801 or 802 that may be toggled between establishing fluid communication between common port 550 one of port A or port B. According to some example embodiments, male connector 735 of an adaptor, e.g. adaptor 710 or 720 is configured to selectively press piston 520 against a spring 530 to establish a flow connection between valve housing block 705 and the adaptor. An O-ring 526 may be pressed against an inner wall of female connector 740, so that flow through a central drill of piston 525 is confined to flow through male connector 735 while the adaptor is connected. As long as male connector 735 does not push piston toward valve housing block 705, corresponding common port 550 and port A are fluidly connected. Based on pushing piston 520 inwards, flow communication is established between common port 550 and the adaptor while flow communication with port A may be blocked. Three-way valve 801 may be configured to toggle flow between an internal and external exhalation valve and three-way valve 802 may be configured toggle flow between an internal and external sampler. Optionally, construction of three-way valve 801 and 802 is identical.

Figure 13:
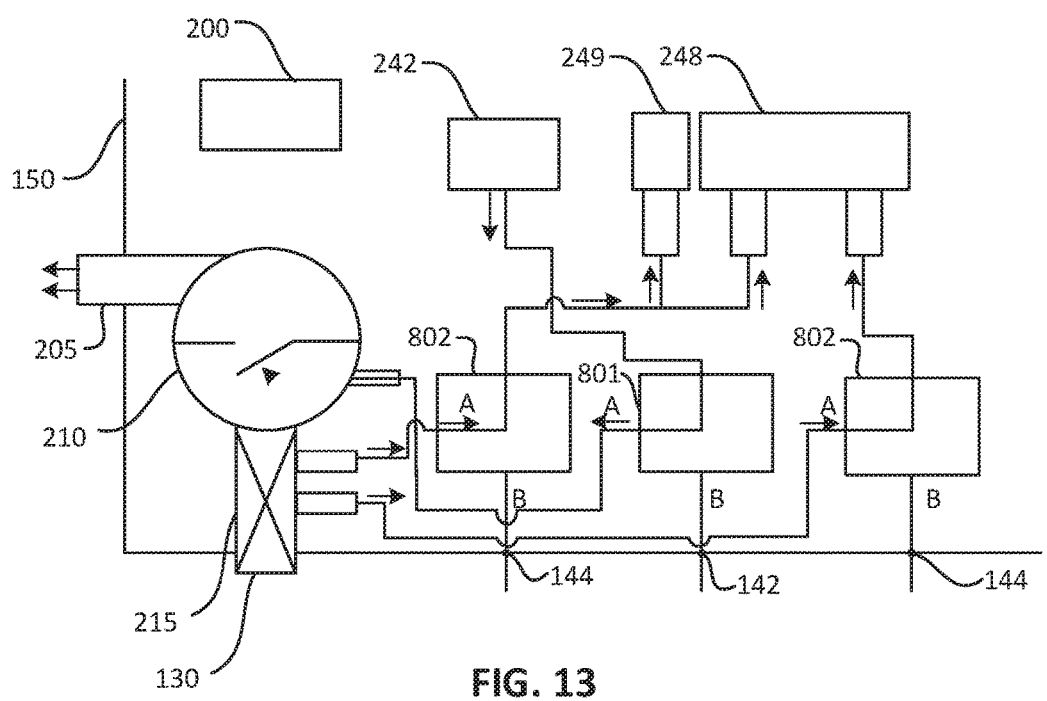
FIG. 13 is exemplary air pathway block diagram including an alternate arrangement of the internal pressure and flow measurements and internal exhalation valve control in accordance with some embodiments of the present disclosure. In some example embodiments.

FIG. 13 is exemplary air pathway block diagram including an alternate arrangement of the internal pressure and flow measurements and internal exhalation valve control in accordance with some embodiments of the present disclosure. In FIG. 13, three-way valves 802 are in place of three-way valves 102 (in FIGS. 1B, 2B and 3B) and three-way valve 801 is in place of three-way valve 101 (in FIGS. 1B, 2B and 3B). A further difference is that pneumatic diaphragm pressure port 142 is positioned between two ports 144 to correspond to position of tube connectors 730 in the adaptor, e.g. adaptor 710 and 720 while maintaining same overall functionality of the system.

Figure 14A:
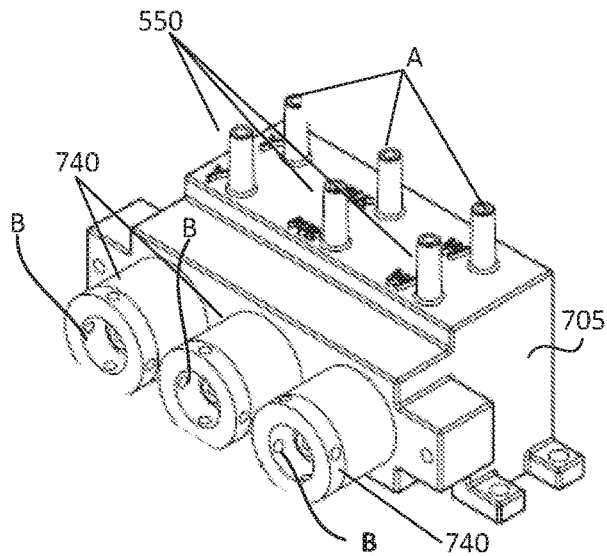
FIGS. 14A, 14B and 14C are perspective and two cross-sectional views of an exemplary valve housing block in accordance with some embodiments of the present disclosure.
Figure 14B:
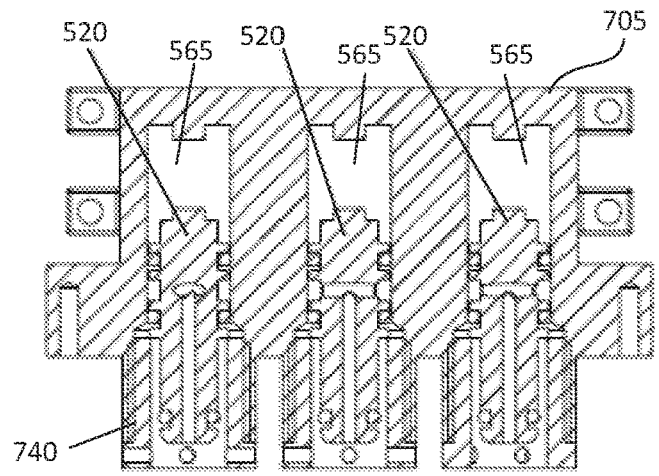
Figure 14C:
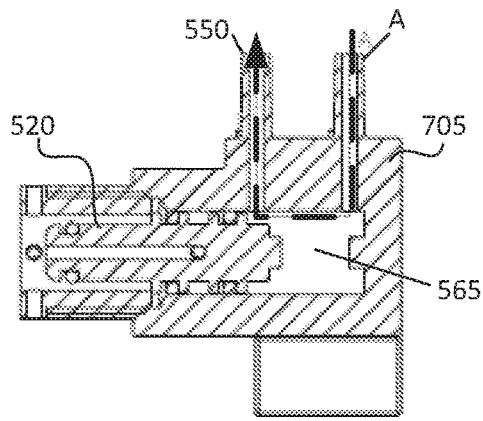

Reference is now made to FIGS. 14A, 14B and 14C showing a perspective and two cross-sectional views of an exemplary valve housing block in accordance with some embodiments of the present disclosure. In some example embodiments, while no adaptor is connected to valve housing block 705, each of pistons 520 is in their neutral position and pressure or flow in valve housing 565 is between a common port 550 and port A. Common port 550 may connect to pressurized air source 242 (FIG. 13) in three-way valve 801 and may connect to delta pressure sensor 248 (FIG. 13) and/or to pressure sensor 249 (FIG. 13) in three-way valve 802. Port A may be connected to internal exhalation valve 210 (FIG. 13) in three-way valve 801 and to an internal sampler 215 (FIG. 13) in three-way valve 802.

Figure 15A:
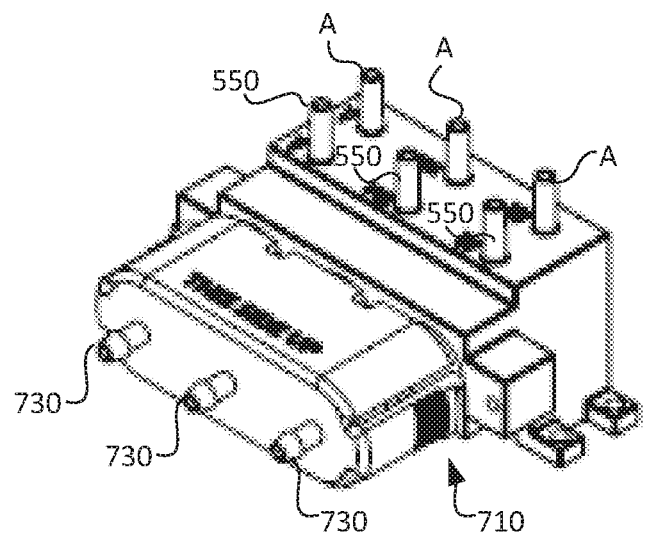
FIGS. 15A, 15B and 15C are perspective and two cross-sectional views of an exemplary patient circuit adaptor connected to an exemplary valve housing block of a ventilator console in accordance with some embodiments of the present disclosure.
Figure 15B:
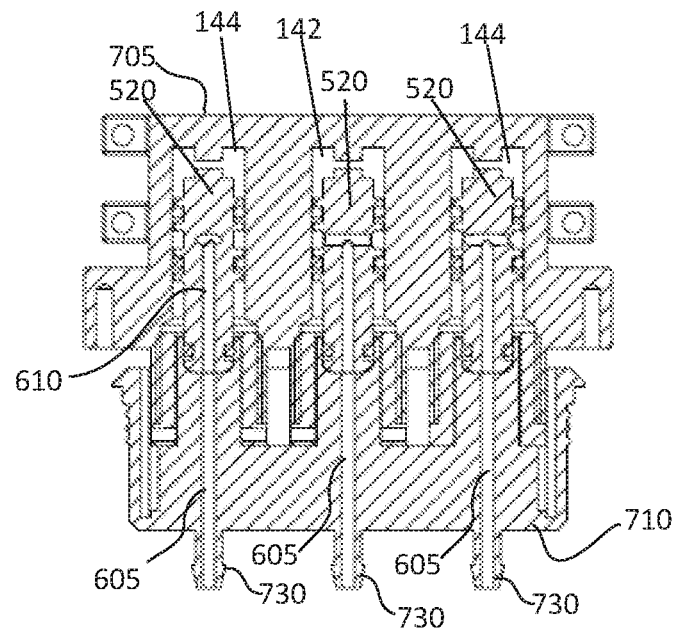
Figure 15C:
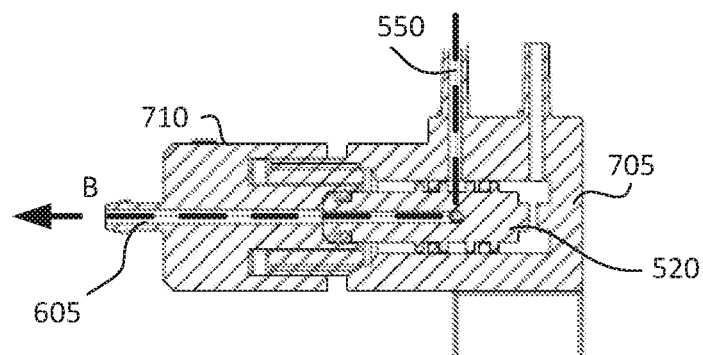

Reference is now made to FIGS. 15A, 15B and 15C showing a perspective and two cross-sectional views of an exemplary patient circuit adaptor connected to an exemplary valve housing block of a ventilator console in accordance with some embodiments of the present disclosure. According to some example embodiments, an adaptor 710 with three tube connectors 730 (and corresponding male connectors 735) is attached to valve housing block 705. Male connectors 735 are configured to push each of pistons 520 further into housing 565 to block pressure or flow between common port 550 and port A and instead establish pressure or flow communication between common port 550 and port B. Flow through piston 520 is as described for example in reference to FIG. 8B. Each of pistons 520 are toggled simultaneously based on connecting adaptor 710 to valve housing block 705, e.g. included in ventilator console 51.

Reference is now made to FIGS. 16A and 16B showing a perspective and cross-sectional views of another exemplary patient circuit adaptor connected to an exemplary valve housing block of a ventilator console in accordance with some embodiments of the present disclosure. According to some example embodiments, an adaptor 720 with two tube connectors 730 (and corresponding male connectors 735) is attached to valve housing block 705. Male connectors 735 are configured to push two out of the three pistons 520. Based on the construction of adaptor 720, piston 520 associated with port 142 (FIG. 13) is left in its neutral position. The other two pistons 520 are pushed further into housing 565 to block pressure or flow between common port 550 and port A and instead establish pressure or flow communication between common port 550 and port B. Flow through the two pistons 520 that are being pushed is as described for example in reference to FIG. 8B. Flow communication between piston 520 associated with port 142 and common port 550 is blocked. Each of pistons 520 are toggled simultaneously based on connecting adaptor 710 to valve housing block 705, e.g. included in ventilator console 51.

Reference is now made to FIGS. 17A and 17B showing perspective and top views respectively of an exemplary patient circuit adaptor plugged into an exemplary ventilator console in accordance with some embodiments of the present disclosure. In some example embodiments, ventilator console 151 (or valve housing block) includes notches, pins or protrusions 736 that are sized and positioned to fit into the corresponding recesses 715 on one of the surfaces of the adaptor, e.g. adaptor 710 or adaptor 720. The number of protrusions 736 may correspond to the number of recesses 715 in the adaptor. According to some example embodiments, recesses 715 with corresponding pins 736 provide a safety mechanism to ensure that the adaptor is connected to the console in the correct orientation, e.g. right side up. It is appreciated that other mechanisms for ensuring that the adaptor may only be fitted on the ventilator console in a desired orientation is also contemplated.

In some example embodiments, ventilator console 151 (or valve housing block) additionally includes notches, pins or protrusions 728 that are configured press against clips 725 and thereby hold the adaptor (adaptor 710 or adaptor 720) in place. It is appreciated that other mechanisms for clipping or securing the adaptor to the ventilator console are possible.

Reference is now made to FIGS. 18A and 18B showing a kit for each of a single-limb and dual-limp patient circuit in accordance with some example embodiments. Kit 910 includes a package 915 for a single-limb patient circuit. Kit 910 may then be connected to a standard exhalation limb 123 and inhalation limb 126 (FIG. 3A). According to some example embodiments, kit 910 includes an adaptor 710 connected to three tubes 920 and an external sampler 280. Optionally in packaging 915, the three tubes 920 are attached at one end to adaptor 710. On an opposite end, the middle tube is to be connected to an external exhalation valve 310, while the lateral tubes are already connected to external sampler 280.

Kit 960 includes a package 915 for a dual-limb patient circuit. According to some example embodiments, kit 960 includes an adaptor 720 connected to two tubes 920 and an external sampler 280. Optionally, the two tubes 920 are attached to adaptor 720 in packaging 915. Similarly, kit 916 may then be connected to a standard exhalation limb 123 and inhalation limb 126 (FIG. 2A).

Reference is now made to FIGS. 19A and 19B showing a kit including a full single-limb and dual-limp patient circuit respectively, both in accordance with some example embodiments. Kit 911 includes a package 915 for a single-limb patient circuit. According to some example embodiments, kit 911 includes an adaptor 710 connected to three tubes 920 and an external sampler 280, as well as an external exhalation valve 310, exhalation limb 123 and inhalation limb 126. Kit 911 is an example of a complete single-limb patient circuit.

Similarly, kit 961 includes a package 915 for a dual-limb patient circuit. According to some example embodiments, kit 961 includes an adaptor 720 connected to two tubes 920, external sampler 280, exhalation limb 123 and inhalation limb 126. Optionally, the two tubes 920 are attached to adaptor 720 in packaging 915. Kit 961 may be an example of a complete dual-limb patient circuit.

Reference is now made to FIG. 20 showing a simplified flow diagram of another exemplary method for switching a patient circuit for a ventilator in accordance with some embodiments of the present disclosure. According to some example embodiments, an operator of a medical ventilator may actuate one of a dual-limb or single-limb circuit with a one plug motion. In some example embodiments, an operator selects a patient circuit kit (block 970). The kit may include a dedicated adaptor that is already connected to tubing and optionally at least a portion of the tubing is connected at an opposite end to an external sampler. A selection of patient circuit kit may include a dual-limb patient circuit and a single-limb patient circuit, each with a dedicated adaptor. An operator may then activate the ventilation (block 980) to obtain ventilation based on the control and sensing as selected. Switching to operation with a different patient circuit may be based on unplugging the adaptor and replacing the patient circuit (block 985). In some example embodiments, switching circuits is based on replacing an entire patient circuit such as example circuits shown in FIGS. 19A and 19B or may be based on replacing the adaptors (adaptor 710 or adaptor 720) with accompanying tubing 920 while affecting a seal in the external sampler 280.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

What is claimed is:

1. A ventilator console comprising:
   an inhalation port via which gas is delivered to the patient;
   an exhalation port via which gas exhaled from a patient is received;
   a console sampler configured to sample pressure or flow at the exhalation port;
   at least one sensor configured to sense at least one of pressure and flow velocity; and
   one or more external control ports configured to provide an interface for flow or pressure communication between the at least one sensor and a tube connected to a patient circuit, wherein at least one external control port of said one or more external control ports comprises a three-way valve,
   wherein the three-way valve comprises a common port, and wherein the three-way valve is connected to the at least one sensor via the common port and is configured to toggle between the console sampler and the at least one external control port and thereby toggling between sampling at the exhalation port and receiving a sample through the at least one external control port, wherein the toggling is manually actuated based on pushing or releasing the three-way valve against a spring force.

2. The ventilator console of claim 1, wherein the at least one external control port includes a sensor port, wherein the three-way valve includes a default position and an actuated position and wherein the three-way valve is configured to provide flow or pressure communication between the at least one sensor and the console sampler in the default position.

3. The ventilator console of claim 1, wherein the at least one external control port includes a sensor port, wherein the three-way valve includes a default position and an actuated position and wherein the three-way valve is configured to provide flow or pressure communication between the at least one sensor and an external sampler in the actuated position.

4. The ventilator console of claim 1, wherein the one or more external control ports includes a pair of sensing ports and wherein the at least one sensor includes a delta pressure sensor and pressure sensor and wherein each of the sensing ports includes the three-way valve.

5. The ventilator console of claim 4, wherein each of the three-way valves in the pair includes an element with a unique shape that is configured to provide a dedicated connection between its dedicated tube connector.

6. The ventilator console of claim 1, wherein the toggling is actuated based on plugging or unplugging a dedicated tube connector of the three-way valve into the at least one external control port.

7. The ventilator console of claim 1, comprising:
a pressurized air source;
an internal exhalation valve configured to be controlled with the pressurized air source;
a diaphragm pressure port configured to provide an interface for flow or pressure communication between an external exhalation valve and the pressurized air source; and
an additional three-way valve integrated with the diaphragm pressure port, wherein the additional three-way valve is connected to the pressurized air source via its common port and is configured to toggle between establishing pressure or flow communication with the internal exhalation valve and establishing pressure or flow communication with the external exhalation valve, wherein the toggling is actuated based on plugging or unplugging a tube connector dedicated to the diaphragm pressure port.

8. The ventilator console of claim 1, comprising:
a pressurized air source;
an internal exhalation valve configured to be controlled with the pressurized air source;
a diaphragm pressure port configured to provide an interface for flow or pressure communication between an external exhalation valve and the pressurized air source; and
an additional three-way valve integrated with the diaphragm pressure port, wherein the additional three-way valve is connected to the pressurized air source via its common port and is configured to toggle between establishing pressure or flow communication with the internal exhalation valve and establishing pressure or flow communication with the external exhalation valve, wherein the toggling of the a three-way valve and the additional three-way valve is based on plugging or unplugging a dedicated adaptor configured to selectively toggle the three-way valve and the additional three-way valve, wherein the selective toggling is of all the three-way valves is performed simultaneously based on the plugging or the unplugging of the dedicated adaptor.

9. The ventilator console of claim 8, wherein the one or more external control ports includes two external control ports each housing a three-way valve and wherein the adaptor is configured to simultaneously toggle the three-way valve in each of the two external control ports.

10. The ventilator console of claim 1, comprising a console controller, wherein the console controller is configured to automatically switch without user intervention between internally and externally controlled breathing based on sensing toggling of the three-way valve.

11. A method for operating a medical ventilator, the method comprising:
selectively plugging in a pair of tube connectors to a pair of flow sensor ports in a ventilator console, wherein each of the flow sensor ports comprises a three-way valve;
selectively plugging in a third tube connector to a pneumatic diaphragm pressure port on the ventilator console, wherein the pneumatic diaphragm pressure port comprises a third three-way valve;
operating the ventilator based on external pressure or flow measurements as long as the pair of tube connectors is plugged into sensing ports;
operating the ventilator based on internal pressure or flow measurements as long as the pair of tube connectors is unplugged to the sensing ports;
operating the ventilator based on an external exhalation valve as long as the third tube connector is plugged into the pneumatic diaphragm pressure port;
operating the ventilator based on an internal exhalation valve as long as the pair of tube connectors is unplugged to the pneumatic diaphragm pressure port;
wherein switching between the different modes of operation is actuated based on the plugging and the unplugging and without interfacing with an electronic display and selecting buttons or dials on the console.

12. The method of claim 11, wherein the switching is performed during ventilation without interrupting the ventilation.

13. The method of claim 11, wherein the tube connectors are connected to tubes on a patient circuit.

14. An adaptor for operating a medical ventilator, wherein the medical ventilator comprises a plurality of three-way valves, comprising:
a housing configured to be attached to a ventilator console, wherein the ventilator console is according to claim 1;
at least two tube connectors extending from the housing;
at least two male connectors each including a central drill, wherein each of the at least two male connectors is fluidly connected to one of the at least two tube connectors and wherein each of the at least two male connectors is shaped and sized to toggle between the console sampler and the at least one external control port and thereby toggling between sampling at the exhalation port and receiving a sample through the at least one external control port, wherein the toggling is manually actuated based on pushing or releasing the adaptor.

15. The adaptor according to claim 14, wherein the at least two male connectors are positioned to penetrate into a pair of sensing ports and to actuate external sensing based on attaching the housing onto the ventilator console.

16. The adaptor according to claim 15 configured to actuate a dual-limb patient circuit based on attaching the housing to the ventilator console.

17. The adaptor according to claim 14, wherein the at least two male connectors includes a third male connector fluidly connected to a third tube connector and wherein the third male connector is positioned to penetrate into a pneumatic diaphragm pressure port based on attaching the housing to the ventilator console.

18. The adaptor according to claim 14 configured to actuate a single-limb patient circuit based on attaching the housing onto the ventilator console.

19. The adaptor according to claim 14, comprising a mechanical feature configured to restrict attachment of the adaptor onto ventilator console to a single orientation.

20. A patient circuit kit for a dual-limb patient circuit comprising:
   an adaptor according to claim 16;
   an external sampler; and
   tubing connecting the tube connectors on the adaptor to the external sampler.

21. A patient circuit kit for a single-limb patient circuit comprising:
   an adaptor according to claim 17;
   an external sampler; and
   tubing connecting a pair of tube connectors on the adaptor to the external sampler and connecting another tube connector to an external exhalation valve.

22. A patient circuit kit according to claim 20, comprising an inhalation limb and an exhalation limb.

23. The ventilator console of claim 1, wherein the at least one sensor comprises an internal sensor of the ventilator.

24. The ventilator console of claim 1, wherein the three-way valve is configured to toggle flow between an internal and external sampler.

* * * * *